US006689160B1

(12) United States Patent
Okuda et al.

(10) Patent No.: US 6,689,160 B1
(45) Date of Patent: Feb. 10, 2004

(54) PROSTHESIS FOR BLOOD VESSEL

(75) Inventors: Yasuhiro Okuda, Osaka (JP); Koichiro Natori, Osaka (JP); Fumihiro Hayashi, Osaka (JP); Toshihiko Kumada, Tokyo (JP); Toshiya Nishibe, Hokkaido (JP); Hidehiko Miura, Hokkaido (JP)

(73) Assignee: Sumitomo Electric Industries, Ltd., Osaka (JP)

( * ) Notice: Subject to any disclaimer, the term of this patent is extended or adjusted under 35 U.S.C. 154(b) by 0 days.

(21) Appl. No.: 09/980,094

(22) PCT Filed: May 30, 2000

(86) PCT No.: PCT/JP00/03469

§ 371 (c)(1),
(2), (4) Date: Nov. 30, 2001

(87) PCT Pub. No.: WO00/72894

PCT Pub. Date: Dec. 7, 2000

(30) Foreign Application Priority Data

| May 31, 1999 | (JP) | ............ | 11/151963 |
| Jul. 28, 1999 | (JP) | ............ | 11/214097 |
| Sep. 3, 1999 | (JP) | ............ | 11/249786 |
| Sep. 20, 1999 | (JP) | ............ | 11/266269 |

(51) Int. Cl.[7] .................................................. A61F 2/06
(52) U.S. Cl. ..................................... 623/1.39; 623/1.44
(58) Field of Search ........................... 623/1.23, 1.24, 623/1.27–1.54

(56) References Cited

U.S. PATENT DOCUMENTS

| 4,187,390 A | 2/1980 | Gore |
| 4,306,318 A | 12/1981 | Mano et al. |
| 4,743,480 A | 5/1988 | Campbell et al. |
| 5,466,509 A | 11/1995 | Kowligi et al. |
| 5,591,225 A | * 1/1997 | Okuda ................ 623/1.49 |
| 5,645,915 A | 7/1997 | Kranzler et al. |
| 5,788,626 A | 8/1998 | Thompson |
| 6,053,939 A | * 4/2000 | Okuda et al. ......... 623/1.43 |

FOREIGN PATENT DOCUMENTS

| EP | 0 232 543 A | 8/1987 |
| GB | 1506432 | 4/1978 |
| JP | 50-135894 | 10/1975 |
| JP | 60-37734 | 8/1985 |
| JP | 60-56619 | 12/1985 |
| JP | 5-84292 | 4/1993 |
| JP | 6-277273 | 10/1994 |
| JP | 7-15022 | 2/1995 |
| JP | 9-241412 | 9/1997 |

OTHER PUBLICATIONS

Golden et al., Journal of Vascular Surgery, "Healing of Polyterafluoroethylene Arterial Grafs is Influenced by Graft Porosity", Jun. 1990, vol. 11, pp. 838–845.*

"Healing of polytetrafluoroethylene arterial grafts is influenced by graft porosity", Golden et al., Journal of Vascular Surgery, vol. 11, No. 6, pp. 838–845, Jun., 1990.

* cited by examiner

Primary Examiner—Corrine McDermott
Assistant Examiner—Hieu Phan
(74) Attorney, Agent, or Firm—McDermott, Will & Emery

(57) ABSTRACT

A prosthesis for a blood vessel, which is an expanded porous polytetrafluoroethylene tube having a fine fibrous structure with nodes connected to each other by fibrils. The average fibril length is at least 40 $\mu$m, and the tube has a porosity of at least 70%. The load required for compressing the tube by 10% in its axial direction at a strain rate of 100%/min is at least 10 gf. The resistant force per unit sectional area of the tube produced upon the 10% compression is at least 1.0 gf/mm$^2$.

13 Claims, 4 Drawing Sheets

PROSTHESIS FOR BLOOD VESSEL

TECHNICAL FIELD

The present invention relates to a prosthesis for a blood vessel, which is composed of an expanded porous polytetrafluoroethylene (i.e., a stretched polytetrafluoroethylene) tube manufactured by stretching process using a polytetrafluoroethylene (PTFE) as a raw material. And more particularly to a prosthesis for a blood vessel which is excellent in mechanical properties and histocompatibility and exhibits good patency even when its inner diameter is as small as less than 6 mm, particularly at most 5 mm, more particularly at most 4 mm. The prosthesis for a blood vessel includes a vascular prosthesis, a covering material of a covered stent, etc. and may hereinafter be referred to as "vascular prosthesis" which is representative thereof.

BACKGROUND ART

Prostheses for blood vessels typified by vascular prostheses are used as a substitute for a lesion part of a vital blood vessel, a prosthesis for a defective part, a bypass for going around the lesion part to maintain blood flow, a conduit for shunting an artery to a vein, etc. As materials for the vascular prostheses, are used, for example, porous PTFE tubes manufactured by a stretching process, woven fabrics and knitted webs of polyester fibers, etc. The vascular prostheses are required to have antithrombogenicity and histocompatibility, since blood flows through their lumina, and they are often implanted in vivo for use by substitution implantation, bypass implantation or the like.

Among the vascular prostheses, a vascular prosthesis composed of an expanded porous PTFE tube (hereinafter referred to as "a porous PTFE vascular prosthesis") is excellent in antithrombogenicity and histocompatibility and hence used widely. The features of the porous PTFE vascular prosthesis reside in that first of all the PTFE itself of a material is excellent in antithrombogenicity. Therefore, the porous PTFE vascular prosthesis is excellent in antithrombogenicity.

Second, the porous PTFE vascular prosthesis has a fine fibrous structure comprising a number of fine fibers (i.e., fibrils) and nodes interconnected with one another by said fibrils. This fine fibrous structure forms a porous structure composed of communicable pores. The porous structure composed of such a fine fibrous structure itself is excellent in affinity for the vital tissue, and the vital tissue penetrates into the porous structure, whereby healing by organization is easy to facilitate.

Third, in the porous PTFE vascular prosthesis, the porous structures such as average fibril length, average pore diameter and porosity, and the forms such as inner diameter and wall thickness may be easily changed by controlling production conditions such as draw ratio upon stretching. Therefore, the porous PTFE vascular prosthesis can cope with various requirements.

As described above, the porous PTFE vascular prosthesis is excellent in antithrombogenicity and histocompatibility and exhibits excellent properties compared with a polyester fiber-made vascular prosthesis. However, although the expanded porous PTFE vascular prosthesis has such excellent properties, when it is provided as a vascular prosthesis having an inner diameter as small as less than 6 mm, particularly at most 5 mm, it occludes in a relatively short period of time after implantation into the vital body so that any good patency cannot be achieved. When occlusion is repeated, the vascular prosthesis must be replaced on that occasion. Therefore, the porous PTFE vascular prosthesis is only put to practical use in a region of the inner diameter of at least 6 mm.

Various techniques have heretofore been proposed in order to improve the patency of the porous PTFE vascular prosthesis. These techniques are roughly divided into (1) a method in which the surface of the porous PTFE vascular prosthesis is modified by, for example, coating the surface with an antithrombogenic substance, thereby improving the antithrombogenicity and histocompatibility thereof, and (2) a method in which the fine fibrous structure constituting the porous structure is modified or optimized, thereby improving the physical properties and/or the histocompatibility thereof. Among these techniques, the method of modifying the surface of the porous PTFE vascular prosthesis is not sufficient in the improving effect by itself, and it is hence desirable to practice it in combination with the method of modifying or optimizing the fine fibrous structure.

The method of modifying or optimizing the fine fibrous structure includes a method in which the average fibril length (distance between nodes) in the fine fibrous structure is lengthened to enlarge the pore diameter of the vascular prosthesis for the purpose of enhancing the penetrability of the vital tissues into the porous structure after implantation of the porous PTFE vascular prosthesis for facilitating healing by organization. Specifically, in Journal of VASCULAR SURGERY, Vol. 11, No. 6, p. 838–845, June (1990), it is reported that a porous PTFE vascular prosthesis, the average fibril length of which has been enlarged to 30 to 60 $\mu$m, particularly about 60 $\mu$m, exhibits a marked healing effect compared with a generally marketed porous PTFE vascular prosthesis the average fibril length of which is about 10 to 30 $\mu$m.

Japanese Patent Application Laid-Open No. 135894/1975 has proposed a porous PTFE vascular prosthesis in which the length of fibrils has been controlled to longer than 5 $\mu$m, preferably longer than 5 $\mu$m, but not longer than 1000 $\mu$m, more preferably 20 to 100 $\mu$m.

According to the result of an implantation experiment by the present inventors, however, it has been found that no sufficient patency is achieved only by enlarging the average fibril length in a small diameter porous PTFE vascular prosthesis having an inner diameter as small as less than 6 mm. The analysis of the reason for it has revealed the following fact.

First, in an expanded porous PTFE tube, the fibrils are strongly oriented in the axial direction of the tube by stretching. Therefore, the rigidity against compression in axial and radial directions of the tube is low though the tensile strength in the axial direction of the tube is high. When the draw ratio upon stretching is made high to enlarge the average fibril length, the rigidity against compression in the axial and radial directions of the tube is further lowered.

When the porous PTFE vascular prosthesis is implanted at a site to which a bending load is applied, a site pressured from surroundings, a site low in blood pressure such as a vein or the like, mechanical pressure is given to the prosthesis, and the prosthesis to become easy constricted. In addition, when the surrounding vital tissue adhered to the outer surface of the porous PTFE vascular prosthesis, or the vital tissue penetrated into the porous wall thereof contracts, the porous PTFE vascular prosthesis tends to be shortened correspondingly. When the porous PTFE vascular prosthesis undergoes deformation such as constriction or shortening, the patency after the implantation into the vital body markedly drops. Such a problem becomes particularly marked when the average fibril length is lengthened, the wall thickness is thinned, or the inner diameter is made small. More specifically, when it is intended to increase the draw ratio upon stretching to enlarge the pore diameter (fibril length) for the purpose of enhancing the affinity for the vital tissue, there arises a problem that the rigidity of the expanded porous PTFE tube is further lowered to fail to apply it to a vascular prosthesis.

In order to solve the problem that the rigidity of the porous PTFE vascular prosthesis against compression in the axial and radial directions thereof is low, there has heretofore been proposed, for example, a method in which reinforcing filaments are wound in the form of a coil or ring around the outer surface of an expanded porous PTFE tube (Japanese Patent Publication Nos. 37734/1985 and 56619/1985). In the method in which the reinforcing filaments are wound around the outer surface of the expanded porous PTFE tube, the reinforcing filaments are wound at a fixed interval to be bonded. Therefore, a difference in rigidity is made between portions reinforced with the filament and portions not reinforced. Accordingly, when the interval at which the reinforcing filaments are wound is in some measure great, the vascular prosthesis is deformed as if it is folded at the portions of the wound reinforcing filaments as flucrums when the vascular prosthesis is bent. As a result, constriction occurs.

It is necessary to closely wind the reinforcing filaments when it is intended to enhance strength against internal pressure, or in order to prevent buckling against pressure from surroundings or bending. When the reinforcing filaments are closely wound, however, penetration of the vital tissue into the porous wall from the surroundings is inhibited by the reinforcing filaments to slow the healing by organization. In addition, the flexibility of the expanded porous PTFE tube is impaired. Therefore, the handling itself becomes difficult. The mere close winding of the reinforcing filaments scarcely achieves an effect to enhance the resistance to the shortening in the axial direction of the tube. Therefore, the shortening of the vascular prosthesis in the axial direction thereof following the contraction of the vital tissue adhered to the outer surface of the vascular prosthesis, or the vital tissue penetrated into the porous wall thereof, cannot be prevented. More specifically, the vascular prosthesis composed of the expanded PTFE tube wounded with the reinforcing filaments causes a phenomenon that it is shortened in the axial direction thereof, it is bended to form thrombus, or the vital tissue formed on the inner wall of the vascular prosthesis peals off or undergoes hypertrophy, thereby it occludes in a short period of time.

In addition, in the vascular prosthesis composed of the expanded PTFE tube wounded with the reinforcing filaments, the reinforcing filaments were an obstacle when suturing the vascular prosthesis to a vital blood vessel. It is therefore necessary to remove the reinforcing filaments at the sutured part. Since the porous PTFE vascular prosthesis is partially broken or deformed by this removing operation itself, thrombus easily forms at the sutured part, the pseudointima of the vital tissue topically undergoes pealing off or hypertrophy. Since rigidity is insufficient at the portion from which the reinforcing filaments have been removed, the shortening of the vascular prosthesis in the axial direction thereof caused by the vital tissue adhered to the outer surface of the vascular prosthesis or the vital tissue penetrated into the porous wall, cannot be prevented. Therefore, the vascular prosthesis is compressed and deformed in the radial direction thereof or contracted in the axial direction thereof, leading to its occlusion in a short period of time.

There has heretofore been proposed a method in which porosity is controlled to at most 60% while enlarging the pore diameter by increasing the draw ratio upon stretching, thereby preventing lowering of compressive rigidity in the axial direction of the tube (Japanese Patent Application Laid-Open No. 277273/1994). According to this method, a porous PTFE vascular prosthesis enlarged in pore diameter can be provided without lowering the rigidity. Since this porous PTFE vascular prosthesis is low in porosity, however, the effect to facilitate the penetration of the vital tissue into the porous wall by the enlarged pore diameter is not sufficiently achieved, and so it tends to occlude in a short period of time. In addition, when the porosity is low, the area ratio of the PTFE resin at the luminal surface increases, so that an anchoring effect by the junction of a pseudointima formed on the luminal surface after implantation to the tissue penetrated into the porous wall becomes insufficient. As a result, the pseudointima is easy to be pealed off by blood flow, resulting in occlusion.

Second, the mere enlargement of the pore diameter of the expanded porous PTFE tube enhances the communicating ability of pores to facilitate the penetration of the vital tissue through the outer surface thereof, but on the other hand, exudation of blood and/or serum from the outer surface is easy to occur when the communicating ability of the pores is enhanced in excess, which is the cause that shows a strong tendency to cause adhesion of surrounding tissue to lead to occlusion.

As a means for avoiding the excessive communicating ability of the pores caused by the enlarged pore diameter, there is considered a method in which the structures of fibrils and nodes forming the fine fibrous structure are improved. However, the structure of the fibrils is as simple as a fine filament connecting nodes with each other. Therefore, it can be only expected that the communicating ability of the pores is slightly changed by, for example, enlarging the fibril diameter or raising the fibril density. However, it is extremely difficult to control the fibril diameter and fibril density while lengthening the average fibril length to enlarge the pore diameter.

On the other hand, It has been known that the structure of the nodes can be controlled to same extent. For example, Japanese Patent Publication No. 15022/1995 discloses a process comprising using an extrusion tip or die having a spiral groove in an extrusion process to extrude PTFE into a tube and then stretching the PTFE tube, thereby producing a expanded porous PTFE tube in which substantially all nodes are oriented at an angle of 85° to 15° to the axis of the tube. Examples of this publication show not only those having an average fibril length as short as 10 to 22 $\mu$m, but also those having an average fibril length as long as 76 $\mu$m.

However, the expanded porous PTFE tubes described in this publication are different from the conventional products only in that the nodes are oriented at one or plural angles to the axis thereof, and the fine fibrous structure itself is unchanged. More specifically, this process is not basically a process devised for controlling the communicating ability of the pores. Therefore, exudation of blood and/or serum from the outer surface due to the enlarged pore diameter can be reduced. Accordingly, this process does not contribute to the improvement in patency.

DISCLOSURE OF THE INVENTION

It is an object of the present invention to provide a prosthesis for a blood vessel, which is manufactured from an expanded porous PTFE tube having a fine fibrous structure comprising fibrils and nodes connected with one another by said fibrils, has a long average fibril length, a large pore diameter, a high porosity, a excellent effect to facilitate penetration into the vital tissue and sufficient rigidity against compression in axial and radial directions thereof even without reinforcing it and is markedly improved in patency after its implantation into a vital body.

Another object of the present invention is to provide a prosthesis for a blood vessel, which is manufactured from an expanded porous PTFE tube having a small diameter in particular and is markedly improved in patency after its implantation into a vital body.

The present inventors have carried out an extensive investigation with a view toward achieving the above objects. As a result, it has been found that even a prosthesis for a blood vessel manufactured from an expanded porous PTFE tube having an average fibril length as long as at least 40 $\mu$m and a porosity as high as at least 70% exhibits excellent patency over a long period of time after its implantation so far at the tube requires a load of a certain value or higher for compressing it in its axial direction and produces a resistant force of a certain value or higher at that time.

It has been further found that when nodes in the fine fibrous structure of the above-described expanded porous PTFE tube have a particular structural feature, exudation of blood and/or serum from its luminal surface can be effectively prevented even when the tube has a large pore diameter and a high porosity. The present invention has been led to completion on the basis of these findings.

According to the present invention, there is thus provided a prosthesis for a blood vessel, which is manufactured from an expanded porous polytetrafluoroethylene tube having a fine fibrous structure comprising fibrils and nodes connected with one another by said fibrils, wherein the tube has the following features:

(A) the average fibril length being at least 40 $\mu$m;

(B) the porosity being at least 70%;

(C) a load required for compressing the tube by 10% in its axial direction at a strain rate of 100%/min being at least 10 gf; and (D) a resistant force per unit sectional area of the tube produced upon the 10% compression being at least 1.0 gf/mm$^2$.

BEST MODE FOR CARRYING OUT THE INVENTION

Figure 1:
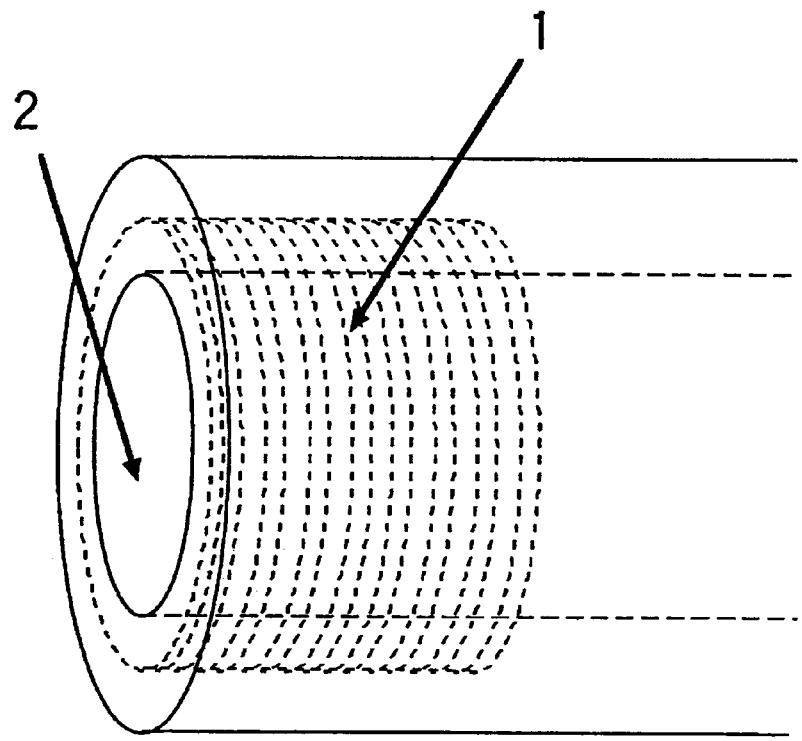
FIG. 1 is a perspective view illustrating a cylindrical curved surface concentric with a luminal surface of an expanded PTFE-made vascular prosthesis.

An expanded porous PTFE tube can be manufactured in accordance with a process in which a liquid lubricant is mixed into unsintered PTFE powder, the resultant mixture is extruded through a ram extruder into a tubular form, and the tubular extrudate is then stretched in its axial direction. After the stretching, the stretched tube is heated to a temperature not lower than the melting point of PTFE while fixing it so as not to undergo shrinkage, thereby sintering and setting the stretched structure. When the stretching temperature of the tubular extrudate is sufficiently high, sintering and setting are made at the same time as completion of the stretching step.

According to such a stretching process, an expanded porous PTFE tube having a fine fibrous structure comprising fibrils and nodes connected with one another by the fibrils is obtained. The fibrils are oriented in a stretching direction (axial direction of the tube), while the nodes are oriented in a direction (circumferential direction of the tube) perpendicular to the stretching direction. This expanded porous PTFE tube is used as a vascular prosthesis as it is, or through various treatments such as a surface treatment with an antithrombogenic substance or the like, formation of a multi-layer structure, and a combination with a reinforcing material. By controlling a draw ratio upon stretching, porous structures such as fibril length (distance between nodes), pore diameter and porosity may be variously changed.

In the porous PTFE vascular prosthesis according to the present invention, the average length of fibrils (average length between nodes) in the fine fibrous structure is at least 40 $\mu$m, preferably 40 to 90 $\mu$m, more preferably 45 to 85 $\mu$m, particularly preferably 50 to 80 $\mu$m. If the average fibril length is too short, any vascular prosthesis exhibiting good patency over a long period of time cannot be provided, and a patent rate after its implantation becomes poor. If the average fibril length is too long, the resulting vascular prosthesis shows a tendency to lower its structural strength. In order to enhance the penetrability of the vital tissue into the porous wall of the vascular prosthesis to facilitate the healing by organization and achieve a good patent result, it is desirable to control the average fibril length within the above range.

In the porous PTFE vascular prosthesis according to the present invention, the distribution of the fibril length is of the order of preferably at least 40%, more preferably 40 to 70%, particularly preferably 45 to 60%. The distribution of the fibril length is expressed as % by dividing the standard deviation of the fibril length by the average fibril length. When the distribution of the fibril length falls within the above range, high patency and healing ability are easy to be achieved.

In the porous PTFE vascular prosthesis according to the present invention, the average length of the nodes is preferably greater than the average fibril length, particularly preferably at least 3 times as much as the average fibril length. When the average length of the nodes is great, the nodes become present in a continuous state, and a fine structure free of orientation in a particular direction is easy to be formed.

In the porous PTFE vascular prosthesis according to the present invention, the porosity is at least 70%, preferably 70 to 90%, more preferably 75 to 85%. If the porosity is too low, the effect to facilitate the penetration of the vital tissue into the porous wall by the enlarged average fibril length is not sufficiently achieved, and so the vascular prosthesis tends to occlude in a short period of time. In addition, when the porosity is low, the area ratio of the PTFE resin at the luminal surface of the vascular prosthesis increases, so that an anchoring effect by the junction of a pseudointima formed on the luminal surface after implantation to the tissue penetrated into the porous wall becomes insufficient. As a result, the pseudointima is easy to be pealed off by blood flow or the like, leading to occlusion in a short period of time. If the porosity is too high, the resulting vascular prosthesis shows a tendency to lower its structural strength.

In general, a porous PTFE vascular prosthesis cannot achieve sufficient mechanical properties when its average fibril length is long and the porosity is high. Therefore, in the present invention, dimensional strength against pressure by the surrounding tissue after implantation and contraction of the tissue penetrated is imparted to the porous PTFE vascular prosthesis itself which is long in average fibril length and high in porosity. By this fact, there can be provided a vascular prosthesis which facilitates the healing by organization by the penetration of the vital tissue into the porous wall of the vascular prosthesis, prevents the formation of thrombus, does not undergo peal off or hypertrophy of the vital tissue formed on the luminal surface (pseudointima), does not apply a tensile load to a host blood vessel and has a high patency rate over a long period of time from the beginning of its implantation into the vital body.

To the vascular prosthesis according to the present invention, can be imparted the dimensional strength against the contraction and pressure without any external reinforcement with reinforcing filaments or the like. When the vascular prosthesis according to the present invention is compared with a vascular prosthesis subjected to a reinforcing treatment, mechanical properties are uniform in the axial direction thereof, so that the flexibility inherent in the expanded porous PTFE tube can be retained. Further, the vascular prosthesis according to the present invention retains high tissue penetrability from the surroundings without impeding the tissue penetrability by reinforcing filaments or the like.

The vascular prosthesis having such excellent properties can be obtained from an expanded porous PTFE tube in which a load required for compressing the tube by 10% in its axial direction at a strain rate of 100%/min is at least 10 gf, preferably 10 to 35 gf, more preferably 11 to 30 gf, particularly preferably 12 to 25 gf, and a resistant force per unit sectional area of the tube produced upon the 10% compression is at least 1.0 gf/mm$^2$, preferably 1.0 to 3.5 gf/mm$^2$, more preferably 1.1 to 3.4 gf/mm$^2$, particularly preferably 1.2 to 3.3 gf/mm$^2$. In many cases, the load required for compressing the tube by 10% in its axial direction at a strain rate of 100%/min is desirably controlled to at least 13 gf. When particularly high rigidity is required against the compression in axial and radial directions of the tube, the resistant force per unit sectional area of the tube produced upon the 10% compression can be controlled to at least 1.5 gf/mm$^2$, further at least 1.7 gf/mm$^2$.

If the load and resistant force defined above are too low, the dimensional strength against pressure by the surrounding tissue after implantation and contraction of the tissue penetrated becomes insufficient, and the shortening or bending of the vascular prosthesis by the contraction of the penetrated tissue is easy to occur, whereby the peal off and hypertrophy of the pseudointima occur to lower the patency. Such a tendency is particularly marked in a vascular prosthesis having an inner diameter as small as less than 6 mm. With respect to the above-described load and resistant force, good results are yielded as their values are greater within a certain range. However, they are limited from the viewpoints of material and production, and such upper limits as described above are taken.

The vascular prosthesis according to the present invention is such that a load per unit length of the tube required for compressing the tube by 10% in a radial direction thereof at a strain rate of 200%/min is preferably at least 15 gf/cm, more preferably 15 to 35 gf/cm, particularly preferably 19 to 33 gf/cm. In many cases, particularly good results can be yielded when this load is at least 20 gf/cm. If the load required for the compression in the radial direction is too low, backling in the radial direction occurs due to the surrounding tissue or bending and hence is easy to occlude, and besides the vascular prosthesis tends to be deformed in the radial direction by a force such as suture tension at a sutured part with the vital tissue, whereby the vascular prosthesis is also easy to lead to occlusion.

When the penetrability of the vital tissue into the porous wall of the vascular prosthesis and the anchoring effect by the junction of the pseudointima formed on the luminal surface after implantation to the tissue penetrated into the porous wall are sufficiently enhanced by lengthening the average fibril length and raising the porosity like the above-described porous PTFE vascular prosthesis, a tendency for exudation of blood and/or serum from the outer surface of the vascular prosthesis to become easy to occur may be observed right after implantation or at an initial stage after the implantation. Such exudation of blood and/or serum from the outer surface of the vascular prosthesis causes adhesion of the vascular prosthesis to the surrounding tissue. The porous PTFE vascular prosthesis is required to be excellent in structural strength and long-term patency in addition to lengthening the average fibril length and raising the porosity.

In order to reduce the exudation of blood and/or serum from the outer surface and enhance the structural strength in addition to lengthening the average fibril length and raising the porosity in the vascular prosthesis composed of the expanded porous PTFE tube, it is effective to improve the structures of the fibrils and nodes forming the fine fibrous structure.

Figure 2:
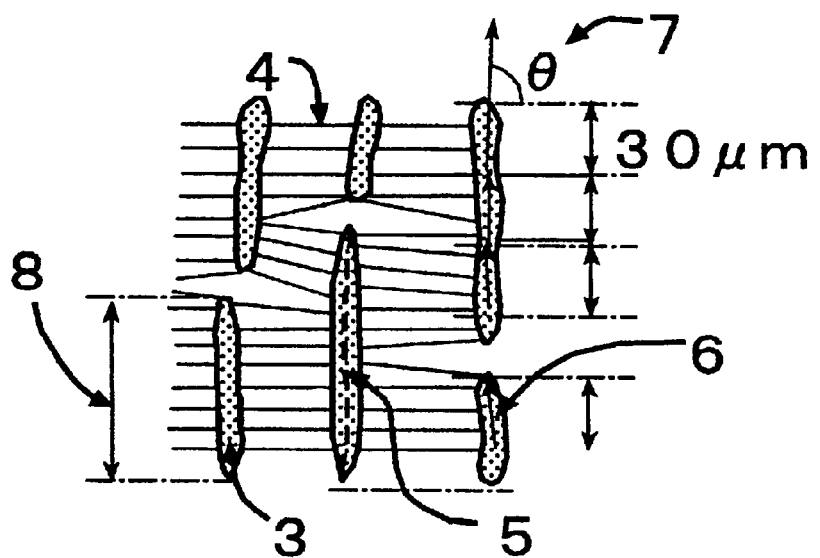
FIG. 2 schematically illustrates a fine fibrous structure of a conventional general expanded PTFE vascular prosthesis.

The conventional expanded porous PTFE tube has a fine fibrous structure comprising fibrils 4 and nodes 3 connected with one another by the fibrils as illustrated in FIG. 2. Since the expanded porous PTFE tube is generally produced by uniaxially stretching a PTFE tube obtained in an extrusion step in its axial direction, the orienting direction of the fibrils consists with the axial direction of the tube. The nodes are generally oriented in a direction perpendicular to the axial direction of the tube. Even when a method of orienting the nodes at a certain angle to the axial direction of the tube (Japanese Patent Publication No. 15022/1995) is adopted, the orienting direction of the fibrils consists with the axial direction of the tube as a result of the uniaxial stretching. In the case of the expanded porous PTFE tube having such a fine fibrous structure as illustrated in FIG. 2, when the draw ratio is raised to lengthen the average fibril length, a distance between nodes is enlarged, and moreover respective nodes are dispersed in such a state that they have been finely cut, so that the structural strength is lowered.

Figure 3:
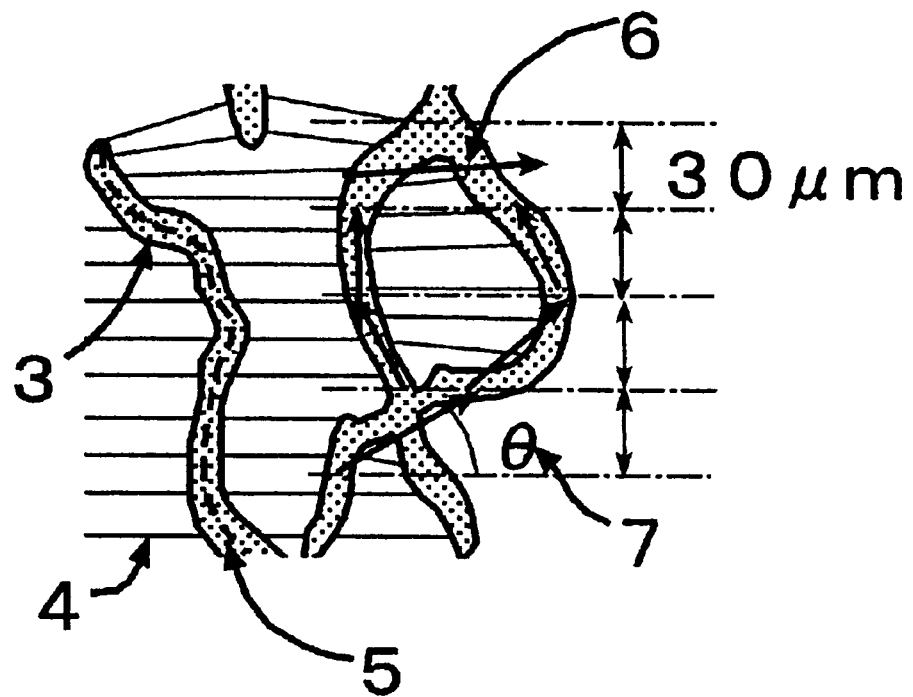
FIG. 3 schematically illustrates a fine fibrous structure of an expanded PTFE vascular prosthesis according to the present invention.

On the other hand, an expanded porous PTFE tube, in which nodes 3 are present in a continuous state and have no orientation in a particular direction, for example, as illustrated in FIG. 3, is excellent in structural strength, and moreover can provide a vascular prosthesis excellent in long-term patency even when its diameter is made small.

The present inventors have investigated the relationship between the form of the fine fibrous structure of a porous PTFE vascular prosthesis and patency in an implantation experiment in detail. As a result, it has been found that when nodes are not oriented in a particular direction, the patency is markedly improved. Specifically, as illustrated in FIGS. 1 to 3, each node on a cylindrical curved surface 1 concentric with an inner periphery (luminal surface) 2 is divided into fine sections of a certain length (for example, 30 µm), an angle (node main axis angle 7) of a main axis 5 of the node in each fine section with a longitudinal axis of the tube body is measured on the luminal surface and outer peripheral surface of the tube and at least 5 cylindrical curved surfaces present between them and concentric with the luminal surface, and the measured node main axis angles are classified into 5 classes within a range of 0 to 180° C. When each class does not exceed ⅖ (40%) of the whole, such a tube becomes a porous PTFE vascular prosthesis markedly excellent in long-term patency even when its bore is small. In FIGS. 2 and 3, referential numeral 6 indicates a direction of a main axis of a node divided (every 30 µm). Referential numeral 8 designates a node length.

When nodes 3 have a branched structure, and the structure is in a form the average number of branchings of which is as many as at least 4.0 per node as illustrated in FIG. 3, the node itself fulfills a part as a structure. As a result, such a tube becomes an expanded porous PTFE vascular prosthesis having high structural strength.

Figure 4:
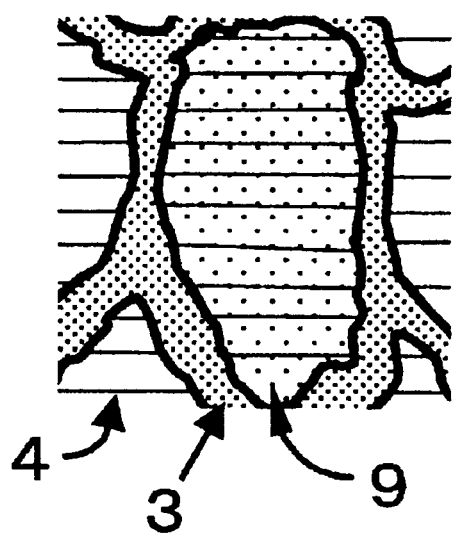
FIG. 4 schematically illustrates an area surrounded by nodes.

When an area 9 surrounded by nodes 3 and an average fibril length have a particular relation as illustrated in FIG. 4, such a tube becomes a vascular prosthesis reduced in exudation of blood and/or serum from the outer surface thereof and improved in structural strength. Even when a node skeleton length and an average fibril length have a particular relation, such a tube becomes a vascular prosthesis excellent in patency.

More specifically, as vascular prostheses reduced in exudation of blood and/or serum from the outer surface thereof and/or improved in structural strength, may be mentioned vascular prostheses manufactured from an expanded porous PTFE tube having such a fine fibrous structure as described below.

First, as a vascular prosthesis reduced in exudation of blood and/or serum from the outer surface thereof, may be mentioned a vascular prosthesis composed of an expanded porous PTFE tube in which in a histogram of 5 classes prepared within a range of 0 to 180° C. as to node main axis angles as measured on the luminal surface and outer peripheral surface of the tube and at least 5 cylindrical curved surfaces present between them and concentric with the luminal surface, each class does not exceed ⅖ in a proportion to the whole. In the histogram, it is more preferable that each class does not exceed ⅓ in a proportion to the whole, particularly preferably 3/10 in a proportion to the whole. In many cases, good results can be yielded when each class in the histogram falls within a range of 1/10 to 3/10 in a proportion to the whole.

Second, as a vascular prosthesis good in structural strength and excellent in long-term patency, may be mentioned a vascular prosthesis composed of an expanded porous PTFE tube in which the average number of branchings of nodes as measured on the luminal surface and outer peripheral surface of the tube and at least 5 cylindrical curved surfaces present between them and concentric with the luminal surface is at least 4.0. The average number of branchings is preferably at least 6.0, more preferably at least 7.0, particularly preferably at least 8.0. No particular limitation is imposed on the upper limit of the average number of branchings. However, it is about 15.0 in many cases.

Third, as a vascular prosthesis reduced in exudation of blood and/or serum from the outer surface thereof and improved in structural strength, may be mentioned a vascular prosthesis composed of an expanded porous PTFE tube in which in a surrounded area graph that an average fibril length (unit=µm) is regarded as an x-axis, and an area (unit=µm²) surrounded by nodes as measured on the luminal surface and outer peripheral surface of the tube and at least 5 cylindrical curved surfaces present between them and concentric with the luminal surface is regarded as a y-axis, the average fibril length and the area surrounded by the nodes fall within a region formed by connecting 3 points of a point A (x=40, y=1000), a point B (x=90, y=1000) and a point C (x=90, y=50000). In the surrounded area graph, it is more preferable that the average fibril length and the area surrounded by the nodes fall within a region formed by connecting 3 points of a point D (x=40, y=2000), a point E (x=80, y=2000) and a point F (x=80, y=40000).

Fourth, as a vascular prosthesis reduced in exudation of blood and/or serum from the outer surface thereof and improved in structural strength, may be mentioned a vascular prosthesis composed of an expanded porous PTFE tube in which in a node skeleton length graph that an average fibril length (unit=µm) is regarded as an x-axis, and a skeleton length (unit=µm) of nodes as measured on the luminal surface and outer peripheral surface of the tube and at least 5 cylindrical curved surfaces present between them and concentric with the luminal surface is regarded as a y-axis, the average fibril length and the node skeleton length fall within a region formed by connecting 5 points of a point H (x=40, y=2000), a point I (x=40, y=400), a point J (x=60, y=200), a point K (x=80, y=200) and a point L (x=80, y=2000). In the node skeleton length graph, it is more preferable that the average fibril length and the node skeleton length fall within a region formed by connecting 5 points of a point, M (x=40, y=2000), a point N (x=40, y=500), a point P (x=60, y=200), a point Q (x=80, y=200) and a point R (x=80, y=2000).

The vascular prostheses composed of the expanded porous PTFE tube according to the present invention are not limited to those obtained by a particular production process. However, they can be preferably produced by a process in which stretching is conducted at a relatively slow average strain rate in a state sufficiently heated at a temperature not lower than the melting point of PTFE in a stretching step to fully shrink the diameter of the tube. After the stretching, it is preferable to conduct an irregularity structure-imparting processing to the outer surface of the tube.

More specifically, a liquid lubricant is first mixed into unsintered PTFE powder, and the resultant mixture is extruded through a ram extruder into a tubular form. The tubular extrudate thus obtained is generally dried to remove the liquid lubricant. The tubular extrudate is then stretched. In the stretching step, the tubular extrudate is stretched in an axial direction (longitudinal direction of the tubular extrudate) of the tube under (1) a dry heat atmosphere of generally 330 to 500° C., preferably 350 to 450° C. at (2) a slow average strain rate of the order of generally 1 to 30%/min, preferably 3 to 25%/min, more preferably 5 to 23%/min and at (3) a draw ratio of generally 3.5 to 10 times, preferably 4 to 9.5 times, more preferably 4.5 to 9 times. The stretching step may be conducted by two or more stages. In this case, it is preferable that PTFE be almost sintered by the stretching of the first stage.

The imparting of the irregularity structure to the outer surface of the expanded porous PTFE tube can be performed by a method of heating the outer surface of the tube obtained in the stretching step with hot air, flame, laser beam or the like. For example, the expanded porous PTFE tube with a stainless steel bar inserted into the lumen thereof and both ends thereof fixed is passed at a fixed rate through an oven with the core temperature kept at about 600 to 1000° C., whereby irregularities can be imparted to the outer surface thereof. The irregularity structure may also be imparted to the outer surface of the expanded porous PTFE tube by a flame treatment by a gas burner or a irradiation treatment with a laser beam.

When the outer surface of the expanded porous PTFE tube is heated, breakage or fusion bonding of the fibrils, fusion bonding of the nodes by contraction between the nodes, and partial decomposition of the surface at the surface portion of the fine fibrous structure occur. As a result, the irregularity structure composed of a great number of fine projected and recessed portions is formed on the whole outer surface. The depth of the recessed portions (i.e., height of the projected portions) is of the order of generally 5 to 80%, preferably 20 to 70%, more preferably 20 to 60% of the wall thickness. A distance between projected portions is of the order of generally 50 to 500 $\mu$m, preferably 100 to 400 $\mu$m. Such a irregularity structure is imparted, whereby a reinforcing effect can be achieved, and histocompatibility and patency are also improved. In the porous PTFE vascular prosthesis to the outer surface of which such an irregularity structure has been imparted, the average fibril length is measured on another fine fibrous structure than the irregularity structure.

The porous PTFE vascular prostheses according to the present invention can be suitably produced by the above-described production process. However, they are not limited to those obtained by the particular production process, since various condition settings and combinations of respective conditions in stretching conditions, conditions for the irregularity structure-imparting treatment, etc. are considered. For example, in the stretching step, there is a process in which the PTFE tubular extrudate is stretched in its axial direction at any given draw ratio without heating it or while suitably heating it, and the stretched tube is then heated at 327° C. which is a sintering temperature of PTFE, or higher while fixing it so as to prevent it from shrinking. In this case, production conditions are independently suitably selected and combined, for example, by raising the heating temperature upon the stretching near to a critical decomposition temperature of PTFE, or lowering the average strain rate upon the stretching, whereby a porous PTFE vascular prosthesis having the desired properties can be produced.

The porous PTFE vascular prostheses according to the present invention have a wall thickness of the order of generally 200 to 1500 $\mu$m, preferably 300 to 1000 $\mu$m. When the irregularity structure is imparted to the outer surface, the wall thickness means a thickness from the inner surface to the top of a projected portion. No particular limitation is imposed on the inner diameter of the porous PTFE vascular prostheses according to the present invention. However, high patency can be retained over a long period of time even when the inner diameter is made as small as less than 6 mm, preferably at most 5 mm, more preferably at most 4 mm. The lower limit of the inner diameter is generally about 1 to 3 mm.

As the porous PTFE vascular prosthesis according to the present invention, the expanded porous PTFE tube obtained above may be used as it is. However, the tube may be subjected to a treatment such as coating of an antithrombogenic substance or a combination with a reinforcing material as needed. However, there is generally no need to conduct the combination with the reinforcing material such as reinforcing fibers.

A leakage pressure (i.e., water entry pressure) of the porous PTFE vascular prostheses according to the present invention is generally at least 0.15 kg/cm$^2$, preferably at least 0.17 kg/cm$^2$. When a particularly high leakage pressure is required, the leakage pressure of the porous PTFE vascular prosthesis according to the present invention can be controlled to at least 0.2 kg/cm$^2$, further at least 0.25 kg/cm$^2$. The leakage pressure means a pressure at the time water droplets leak out of the outer wall of the vascular prosthesis for the first time when a water pressure is gradually applied to the luminal surface of the vascular prosthesis. The leakage pressure is preset great, whereby blood leakage through pores of the porous wall after its implantation can be prevented to enhance patency. The upper limit of the leakage pressure is about 0.35 kg/cm$^2$.

A bubble point of the porous PTFE vascular prostheses according to the present invention is generally at least 0.05 kg/cm$^2$, preferably 0.05 to 0.16 kg/cm$^2$, more preferably 0.06 to 0.15 kg/cm$^2$ as measured with isopropyl alcohol. When the bubble point falls within the above range, penetrability of cells into the wall of the vascular prosthesis from the lumen and the outside can be enhanced, at the same time, exudation of blood and/or serum from the lumen can be effectively reduced.

In order to enhance antithrombogenicity and histocompatibility, the surfaces of the porous PTFE vascular prostheses according to the present invention can be modified by combining them with any of various physiologically active substances, and the patency can be further enhanced. Examples of tissue-derived substance capable of being combined include proteins having cell adhesion, such as collagen, gelatin, laminin and fibronectin; and growth factors having cell proliferativity, such as TGF-α (transforming growth factor α), insulin, transferrin, FGF (fibroblast growth factor), ECGF (endothelial cell growth factor), BPE (brain pituitary extract), PDGF (platelet derived growth factor) and VEGF (vascular endothelial cell growth factor). These substances may be used either singly or in any combination thereof. Among these, fibronectin, TGF-α, insulin, transferrin, FGF and VEGF are preferably used either singly or in any combination thereof.

Examples of antithrombogenic substances capable of being combined include such as anticoagulants such as hirudine, heparin and 4-methyl-1-[N-2-(methyl-1,2,3,4-tetrahydro-8-quinolyl)-sulfonyl]-L-arginyl-2-piperidine carbonic acid (MD805); plasminogen activators such as tissue plasminogen activator (t-PA) and urokinase; fibrinolytic enzymes such as plasmin and subtilisin; and antiplatelets such as prostacyclin, aspirin and ticlopidine. Among these, heparin is particularly preferred.

Methods for combining the expanded porous PTFE tube with the tissue-induced substance or antithrombogenic substance include (1) a method in which the intended substance is simply physically applied to the surface of the tube, and (2) a method in which after the tube is subjected to a defluorination treatment by, for example, a method by a chemical treatment with an alkali metal or a method by a physical treatment such as irradiation of radiation such as γ-rays or electron rays, or a corona discharge or glow discharge treatment, a functional group is introduced by, for example, adding a compound having a carboxyl group, hydroxyl group, amino group, epoxy group or the like in its molecule, and the intended substance is chemically bonded to the functional group. The method of chemically bonding the intended substance to the introduced functional group is preferred so far as the intended substance is a substance which does not lose its activity even by the chemical bonding. As a method therefor, it is only necessary to select a method suitable for the functional group, and particularly to select a method by which the activity of the intended substance is not lost by immobilization.

The porous PTFE vascular prostheses according to the present invention may be not only used as tubes themselves, but also used in combination with other medical instruments as a part thereof, for example, covering materials of covered stents. The porous PTFE vascular prostheses according to the present invention are excellent in compressive rigidity in axial and radial directions thereof. When rigidity is particularly required, however, reinforcement such as rings or spirals with reinforcing fibers can be applied to the outer surfaces thereof. In this case, the reinforcement is not limited to fibers, and tape-like reinforcement may also be effectively used.

EXAMPLES

The present invention will hereinafter be described more specifically by the following Examples and Comparative Examples. Physical properties and properties or characteristics in the following examples were measured in accordance with the following respective methods.

(1) Average Fibril Length and Distribution of Fibril Length

On each of circumferential surfaces obtained by dividing an expanded porous PTFE tube sample into 5 or more pieces at equal intervals in a thickness-wise direction of the wall from the outer surface to the inner surface of the tube, 100 fibrils in order of length, beginning with the longest, were selected through a scanning electron microscope, and their lengths were measured to find an average value (average fibril length) thereof. However, any fibrils having a length of 5 $\mu$m or shorter were omitted from the measurement because a boundary with a node is indefinite. The distribution of the fibril length was expressed as % by dividing the standard deviation of the fibril length by the average fibril length.

(2) Porosity

The porosity of each sample was determined in accordance with ASTM D 792.

(3) Patency Rate

Vascular prosthesis samples having an inner diameter of 4 mm and a length of 4 cm were substitutively implanted into carotid arteries of dogs about 10 kg in weight, and proportions of the number of vascular prosthesis samples, which retained blood flow upon elapsed time of 4 weeks and 12 weeks after the substitution implantation, to the number of the vascular prosthesis samples substituted were calculated out.

(4) Compressive Load in Axial Direction of Tube and Resistant Force Thereto

A specimen was obtained by cutting an expanded porous PTFE tube sample into lengths of 2 cm. The specimen was compressed in its axial direction at a crosshead speed of 20 mm/min (strain rate=100%/min) by means of an autograph manufactured by Shimadzu Corporation while taking care that the tubular specimen is not bent, thereby finding a load (gf) required for compressing the specimen by 2 mm (by 10%) from a displacement-load curve. This load was divided by the sectional area of the tube sample to find a resistant force (gf/mm$^2$) per unit area of the tube.

(5) Compressive Load in Radial Direction

A specimen was obtained by cutting an expanded porous PTFE tube sample into lengths of 2 cm. The specimen was compressed in a radial direction thereof at a crosshead speed of 10 mm/min (strain rate=200%/min) where the outer diameter was 5 mm, 11 mm/min (strain rate=200%/min) where the outer diameter was 5.5 mm or 12 mm/min (strain rate=200%/min) where the outer diameter was 6 mm by means of an autograph manufactured by Shimadzu Corporation, thereby finding a load (gf) required for compressing the specimen by 10% from a displacement-load curve. This load was divided by 2 to regard the resultant value as a compressive load (gf/mm$^2$) in the radial direction per unit length of the tube.

(6) Node Main Axis Angle

A specimen containing the inner surface and the outer surface and having proper widths in axial and circumferential directions of the tube was cut out of an expanded porous PTFE tube sample. This specimen was then pressed with a force to such an extent that the thickness of the tube wall is not changed as much as possible, in such a manner that the inner surface and the outer surface run parallel with each other. The specimen was embedded with paraffin while retaining this form. At least 5 sections coming into contact with the circumference were formed at every 50-$\mu$m thickness from the inner surface to the outer surface of the paraffin-embedded specimen. With respect to the fine structure at almost central part of each section, a photograph in a range 15 times as much as the average fibril length from the axial direction of the tube and of at least 700 $\mu$m in a direction perpendicular to the axial direction was taken through a differential interference microscope (ECLIPSE E600, manufactured by NIKON CORP.) so as to give 100 magnifications on the photograph.

Thereafter, the differential interference microphotograph was taken in a computer at an accuracy of at least 1.5 pixel/$\mu$m in both vertical and lateral directions, i.e., circumferential and axial directions and 256 gradations in a gray scale. Only nodes were extracted from this image using an image analytic program (Win Roof, manufactured by Mitani Shoji K.K.) to form a binary image. A main axis of each node was determined on this binary image. The term "main axis of the node" as used herein means a line connecting the center of a width of each node in the axial direction. Specifically, this is obtained by conducting fine line protocol repeatedly to the image composed of the nodes alone extracted previously on the image analytic program until it is no longer changed.

Thereafter, as to all the nodes, the length of the main axis of which exceeds three times as much as the average fibril length, on a cylindrical curved surface concentric with the inner periphery of the tube, the main axis of each node was divided every 30 $\mu$m in the width of the circumferential direction by the image analytic program, and an angle of a straight line connecting both ends of the main axis in each section with the longitudinal axis of the tube body was measured. This angle was defined as the node main axis angle. All elements of the node main axis angles measured in such a manner were classified into 5 classes equally divided within a range of 0 to 180° to prepare a histogram.

(7) Average Number of Branchings of Node

The total number of branchings of the main axes of the nodes on the differential interference microphotograph on the cylindrical curved surface concentric with the inner periphery of the tube was counted by the above-described image analytic program. At this time, any branching points within a 10-μm radius from each branching point were neglected for the counting because separation was difficult. Thereafter, the total number of the nodes on the same differential interference microphotograph was separately counted, and the total number of the branchings of the main axes previously counted was divided by this total number to find an average number of branchings per node. This value was regarded as the average number of branchings of the node.

(8) Average Node Length

The measurement was conducted in the same process as in the measurement of the node main axis angle until only nodes were extracted to form a binary image. Thereafter, the maximum length of each node was measured on the binary image using an image analytic program (Win Roof, manufactured by Mitani Shoji K.K.). At this time, any nodes having a length of 10 μm or shorter were omitted from the measurement because separation from foreign matter or the like was difficult.

(9) Node Skeleton Length

The measurement was conducted in the same process as in the measurement of the node main axis angle until the main axis of each node was determined. Thereafter, the length of the main axis of each node was measured on the cylindrical curved surface concentric with the inner periphery of the tube by the same image analytic program. At this time, any nodes having a node skeleton length of 5 μm or shorter were omitted from the measurement because separation from foreign matter or the like was difficult.

(10) Area Surrounded by Nodes

The measurement was conducted in the same process as in the measurement of the node main axis angle until only nodes were extracted to form a binary image. Thereafter, the binary image was reversed to select only regions surrounded by the nodes. Thereafter, areas of the regions surrounded by the nodes were separately measured using an image analytic program (Win Roof, manufactured by Mitani Shoji K.K.). An average value of areas of regions having an area of 25 μm² or smaller surrounded by the nodes was then calculated out to regard it as the area surrounded by the nodes.

(11) Cell-penetrated State Within Tube Wall After Removal

A vascular prosthesis sample having a length of 4 cm was substitutively implanted into a carotid artery of a dog about 10 kg in weight. Upon elapsed time of 12 weeks after the substitution implantation, the vascular prosthesis was removed, fixed with formalin and subjected to HE stain to count the number of cells present within the tube wall of the vascular prosthesis. The samples evaluated were classified into 3 ranks of "Excellent (Ex)", "Good (Gd)" and "Unacceptable (Ua)" in order of cells, beginning with the most.

(12) Exudated State of Blood and Serum from the Outer Surface of Vascular Prosthesis A vascular prosthesis sample having a length of 4 cm was substitutively implanted into a carotid artery of a dog about 10 kg in weight. Upon elapsed time of 1 to 4 weeks after the substitution implantation, an amount of blood and serum exudated was estimated from an ultrasonic echo image about the vascular prosthesis. The samples evaluated were classified into 3 ranks of "Great (Gr)", "Small (Sm)" and "None (No)" in order of amount, beginning with the most.

(13) Bubble Point

The bubble point using isopropyl alcohol was determined by immersing a vascular prosthesis sample in isopropyl alcohol to fill the pores in the tube wall with isopropyl alcohol and then slowly introducing air into the lumen of the vascular prosthesis to measure a pressure at the time bubbles came out of the outer surface of the vascular prosthesis for the first time when an air pressure was gradually applied to the luminal surface.

(14) Leakage Pressure

The leakage pressure was determined by measuring a pressure at the time water droplets leaked out of the outer wall surface of a vascular prosthesis sample for the first time when a water pressure was gradually applied to the luminal surface of the vascular prosthesis.

Example 1

After 25 parts by weight of a liquid lubricant (naphtha) were mixed as an auxiliary with 100 parts by weight of PTFE fine powder (product of Daikin Chemical Co., Ltd.), and they were got intimate with each other for at least 24 hours, the mixture was extruded through a ram extruder into a tubular form, and the extrudate was then dried at 60° C. The extruded tube thus obtained was stretched in its axial direction under conditions of an average strain rate of 8%/min in an electric oven preset to a temperature of 350° C. so as to give a length 5.5 times as much as the original length, thereby obtaining an expanded porous PTFE tube. A stainless steel bar having an outer diameter of 4 mm was inserted into the lumen of this expanded porous PTFE tube, and the tube thus treated was passed at a fixed rate through an electric radiating oven with the core temperature preset at 950° C. in a state that both ends of the tube were fixed, whereby an irregularity structure that the depth was 50% of the whole wall thickness and a distance between projected portions was 200 to 300 μm was imparted to the outer surface of the tube.

As a result, a vascular prosthesis made of the expanded porous PTFE tube having an average fibril length of 58 μm, a porosity of 78%, an isopropyl alcohol bubble point (hereinafter referred to as "iPABP") of 0.13 kg/cm², a leakage pressure of 0.26 kg/cm², an inner diameter of 4.0 mm, an outer diameter of 5.0 mm and a thickness of 500 μm at the projected portions was obtained. The melting point of this expanded porous PTFE tube was 327° C. as measured by DSC (differential scanning calorimeter), and the tube was completely sintered.

A 20-mm specimen was cut out of this expanded porous PTFE tube to measure a load required for compressing the tube by 2 mm in its axial direction at a crosshead speed of 20 mm/min. As a result, it was 22 gf. A resistant force per unit sectional area of the tube produced at this time was 3.11 gf/mm². A 10-mm specimen was cut out of this expanded porous PTFE tube to measure a load required for compressing the tube by 10% in its radial direction at a rate of 10 mm/min. As a result, it was 26 gf.

The node main axis angle of this expanded porous PTFE tube was measured. As a result, a maximum peak of a histogram was about 24%, and nodes were almost in a form of a network. The average number of branchings of the nodes in this expanded porous PTFE tube was 8.3 per node.

This expanded porous PTFE tube was cut into lengths of 4 cm to use their pieces as a sample of a vascular prosthesis. Ten samples were substitutively implanted into respective carotid arteries of 10 beagles. After 4 weeks, blood flow was retained in 10 beagles (patency rate=100%), while blood flow was retained in 8 beagles (patency rate=80%) after 12 weeks. The length of the sample removed from each beagle was 4 cm, and so it was not shortened at all, and neither bending nor deformation was observed.

Example 2

An expanded porous PTFE tube was produced in the same manner as in Example 1 except that the average strain rate upon the stretching was changed to 12%, and evaluated likewise. The length of each vascular prosthesis sample upon the removal was 4 cm, and so it was not shortened at all, and neither bending nor deformation was observed.

Example 3

An expanded porous PTFE tube was produced in the same manner as in Example 1 except that the average strain rate upon the stretching was changed to 19%, and evaluated likewise. The length of each vascular prosthesis sample upon the removal was 4 cm, and so it was not shortened at all, and neither bending nor deformation was observed.

Example 4

An expanded porous PTFE tube was produced in the same manner as in Example 1 except that the inner diameter/outer diameter of the extruded tube were controlled in such a manner that the inner diameter/outer diameter of the stretched tube were 4.0 mm/5.5 mm, and the average strain rate and draw ratio upon the stretching were changed to 8% and 5.0 times, respectively, and evaluated likewise. The length of each vascular prosthesis sample upon the removal was 4 cm, and so it was not shortened at all, and neither bending nor deformation was observed.

Example 5

An expanded porous PTFE tube was produced in the same manner as in Example 1 except that the inner diameter/outer diameter of the extruded tube were controlled in such a manner that the inner diameter/outer diameter of the stretched tube were 4.0 mm/6.0 mm, and the average strain rate and draw ratio upon the stretching were changed to 12% and 5.0 times, respectively, and evaluated likewise. The length of each vascular prosthesis sample upon the removal was 4 cm, and so it was not shortened at all, and neither bending nor deformation was observed.

Example 6

An expanded porous PTFE tube was produced in the same manner as in Example 1 except that the average strain rate and draw ratio upon the stretching were changed to 18% and 9.0 times, respectively, and evaluated likewise. The length of each vascular prosthesis sample upon the removal was 4 cm, and so it was not shortened at all, and neither bending nor deformation was observed.

Example 7

After 25 parts by weight of a liquid lubricant (white oil, product of Esso Co.) were mixed as an auxiliary with 100 parts by weight of PTFE fine powder (F104, product of Daikin Chemical Co., Ltd.), and they were got intimate with each other for at least 24 hours, the mixture was extruded through a ram extruder into a tubular form, and the extruded tube thus obtained was dried at 60° C. The dried tube was stretched under conditions of an average strain rate of 12%/min in an electric oven preset to a temperature of 380° C. so as to give a length 6.0 times as much as the original length, thereby obtaining an expanded porous PTFE tube. A stainless steel bar having a diameter of 4 mm was inserted into the lumen of this expanded porous PTFE tube, and both ends of the tube were fixed.

The core surface temperature of an electric radiating oven comprising a quartz glass cylinder having a length of 40 cm and an inner diameter of 35 mm as a reactor core was heated to 950° C. The expanded porous PTFE tube with the stainless steel bar inserted therein was passed at a fixed rate through this oven, whereby an irregularity structure that the depth was 50% of the whole wall thickness and a distance between projected portions was 200 to 300 $\mu$m was imparted to the outer surface of the tube. As a result, an expanded porous PTFE tube having an average fibril length of 60 $\mu$m, a fibril length distribution of 60%, iPABP of 0.10 kg/cm$^2$, a leakage pressure of 0.20 kg/cm$^2$, an inner diameter of 4 mm and a thickness of 700 $\mu$m at the projected portions was obtained.

A 20-mm specimen was cut out of this expanded porous PTFE tube to measure a load required for compressing the tube by 2 mm in its axial direction at a crosshead speed of 20 mm/min. As a result, it was 16 gf. A resistant force per unit sectional area of the tube produced at this time was 1.55 gf/mm$^2$. A 10-mm specimen was cut out of this expanded porous PTFE tube to measure a load required for compressing the tube by 10% in its radial direction at a rate of 10 mm/min. As a result, it was 23.0 gf.

The node main axis angle of this expanded porous PTFE tube was measured. As a result, a maximum peak of a histogram was about 25%, and nodes were almost in a form of a network. The average number of branchings of the nodes in this expanded porous PTFE tube was 13.0 per node.

This expanded porous PTFE tube was cut into lengths of 4 cm to use their pieces as a sample of a vascular prosthesis. This sample was implanted into carotid arteries of 20 dogs. The patency rate after 4 weeks was 100%. According to an ultrasonic echo test about the vascular prosthesis after 1 to 4 weeks, exudation of blood and serum from the outer surface of the vascular prosthesis was slight to such an extent that it was scarcely observed. Even after 12 weeks, blood flow was observed in 18 dogs, and it was hence confirmed that the vascular prosthesis has an extremely high patency rate. This vascular prosthesis was also excellent in penetrated state of cells after its removal. The length of the sample at its removal was 4 cm, and so it was not shortened at all, and neither bending nor deformation was observed.

Figure 5:
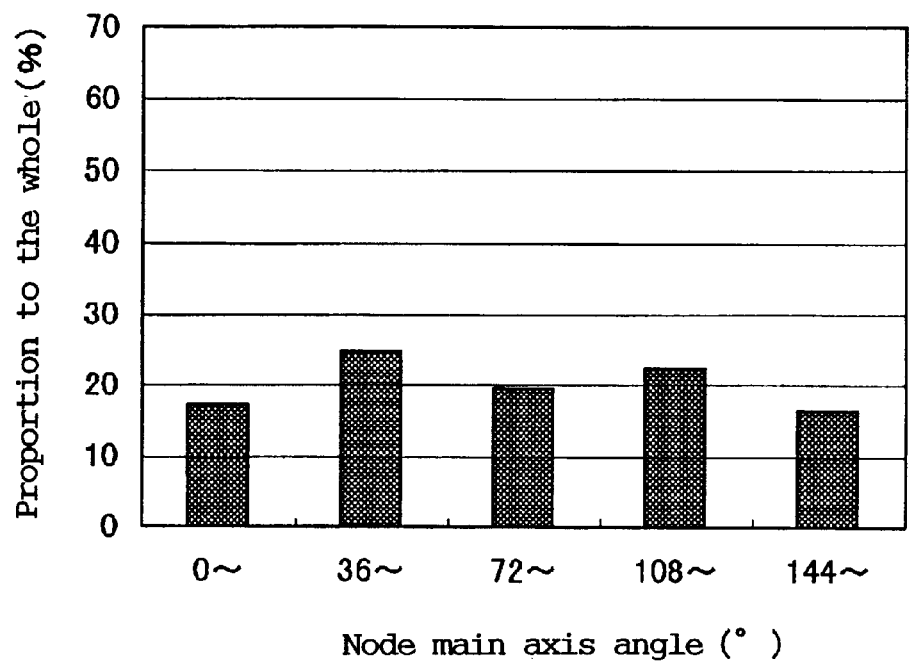
FIG. 5 illustrates a histogram in the case where main axis angles of nodes at 0 to 180° as to an expanded PTFE tube according to Example 7 are divided into classes of every 36 degrees.

With respect to this expanded porous PTFE tube, a histogram where the node main axis angles at 0 to 180° were classified into classes of every 360 is illustrated in FIG. 5.

Example 8

A dried tube was produced in accordance with the same procedure as in Example 7, and the dried tube was then stretched under conditions of an average strain rate of 14%/min in an electric oven preset to a temperature of 380° C. so as to give a length 5.0 times as much as the original length, thereby obtaining an expanded porous PTFE tube. Thereafter, an irregularity structure that the depth was 50% of the whole wall thickness and a distance between projected portions was 200 to 300 μm was imparted to the outer surface of the tube in the same manner as in Example 7. As a result, an expanded porous PTFE tube having an average fibril length of 40 μm, a fibril length distribution of 40%, iPABP of 0.13 kg/cm$^2$, a leakage pressure of 0.30 kg/cm$^2$, an inner diameter of 4 mm and a thickness of 700 μm at the projected portions was obtained.

The node main axis angle of this expanded porous PTFE tube was measured. As a result, a maximum peak of a histogram was about 35%, and the form of nodes was in a state near a network. A vascular prosthesis sample composed of the expanded porous PTFE tube was implanted into carotid arteries of 18 dogs. After 4 weeks, blood flow was observed in 13 dogs. According to an ultrasonic echo test about the vascular prosthesis after 1 to 4 weeks, exudation of blood and serum from the outer surface of the vascular prosthesis was scarcely observed. Even after 12 weeks, blood flow was observed in 9 dogs, and it was hence confirmed that the vascular prosthesis has high patency. This vascular prosthesis was good in penetrated state of cells after its removal.

Example 9

A dried tube was produced in accordance with the same procedure as in Example 7, and the dried tube was then stretched under conditions of an average strain rate of 18%/min in an electric oven preset to a temperature of 380° C. so as to give a length 7.5 times as much as the original length, thereby obtaining an expanded porous PTFE tube. Thereafter, an irregularity structure that the depth was 50% of the whole wall thickness and a distance between projected portions was 200 to 300 μm was imparted to the outer surface of the tube in the same manner as in Example 7. As a result, an expanded porous PTFE tube having an average fibril length of 60 μm, a fibril length distribution of 45%, iPABP of 0.11 kg/cm$^2$, a leakage pressure of 0.25 kg/cm$^2$, an inner diameter of 4 mm and a thickness of 700 μm at the projected portions was obtained.

The node main axis angle of this expanded porous PTFE tube was measured. As a result, a maximum peak of a histogram was about 30%, and the form of nodes was in a state near a network. A vascular prosthesis sample composed of the expanded porous PTFE tube was implanted into carotid arteries of 25 dogs. According to an ultrasonic echo test about the vascular prosthesis after 1 to 4 weeks, exudation of blood and serum from the outer surface of the vascular prosthesis was slight to such an extent that it was scarcely observed. Even after 12 weeks, blood flow was observed in 20 dogs, and it was hence confirmed that the vascular prosthesis has extremely high patency. This vascular prosthesis was also excellent in penetrated state of cells after its removal.

Example 10

A dried tube was produced in accordance with the same procedure as in Example 7, and the dried tube was then stretched under conditions of an average strain rate of 10%/min in an electric oven preset to a temperature of 380° C. so as to give a length 8.0 times as much as the original length, thereby obtaining an expanded porous PTFE tube. Thereafter, an irregularity structure that the depth was 50% of the whole wall thickness and a distance between projected portions was 200 to 300 μm was imparted to the outer surface of the tube in the same manner as in Example 7. As a result, an expanded porous PTFE tube having an average fibril length of 80 μm, a fibril length distribution of 45%, iPABP of 0.06 kg/cm$^2$, a leakage pressure of 0.18 kg/cm$^2$, an inner diameter of 4 mm and a thickness of 700 μm at the projected portions was obtained.

The node main axis angle of this expanded porous PTFE tube was measured. As a result, a maximum peak of a histogram was about 25%, and the form of nodes was in a state near a network. A vascular prosthesis sample composed of the expanded porous PTFE tube was implanted into carotid arteries of 25 dogs. After 4 weeks, blood flow was observed in 20 dogs. According to an ultrasonic echo test about the vascular prosthesis after 1 to 4 weeks, exudation of blood and serum from the outer surface of the vascular prosthesis was slight to such an extent that it was scarcely observed. Even after 12 weeks, blood flow was observed in 15 dogs, and it was hence confirmed that the vascular prosthesis has high patency. This vascular prosthesis was also excellent in penetrated state of cells after its removal.

Example 11

After 25 parts by weight of a liquid lubricant (naphtha) were mixed as an auxiliary with 100 parts by weight of PTFE fine powder (product of Daikin Chemical Co., Ltd.), and they were got intimate with each other for at least 24 hours, the mixture was extruded through a ram extruder into a tubular form, and this extruded tube was then dried at 60° C. to obtain a dried tube. Thereafter, this tube was stretched under conditions of an average strain rate of 13%/min in an electric oven preset to a temperature of 380° C. so as to give a length 6.5 times as much as the original length, thereby obtaining an expanded porous PTFE tube.

Thereafter, a stainless steel bar having a diameter of 4 mm was inserted into the lumen of the expanded porous PTFE tube, and the tube thus treated was passed at a fixed rate through an electric radiating oven with the core temperature preset at 950° C. in a state that both ends of the tube were fixed, whereby an irregularity structure that the depth of recessed portions was 50% of the whole wall thickness and a distance between projected portions was 200 to 300 μm was imparted to the outer surface of the expanded porous PTFE tube. As a result, an expanded porous PTFE tube having an average fibril length of 60 μm, a porosity of 78%, iPABP of 0.10 kg/cm$^2$, a leakage pressure of 0.22 kg/cm$^2$, an inner diameter of 4.0 mm and a thickness of 700 μm at the projected portions was obtained.

A 20-mm specimen was cut out of this expanded porous PTFE tube to measure a load required for compressing the tube by 2 mm in its axial direction at a crosshead speed of 20 mm/min. As a result, it was 13 gf. A resistant force per unit sectional area of the tube produced at this time was 1.26 gf/mm$^2$. A 10-mm specimen was cut out of this expanded porous PTFE tube to measure a load required for compressing the tube by 10% in its radial direction at a rate of 10 mm/min. As a result, it was 23 gf.

The node main axis angle of this expanded porous PTFE tube was measured. As a result, a maximum peak of a histogram was about 15%, and nodes were almost in a form of a network. The average number of branchings of the nodes in this expanded porous PTFE tube was 8.5 per node.

This expanded porous PTFE tube was cut into lengths of 4 cm to use their pieces as a sample of a vascular prosthesis. This sample was implanted into carotid arteries of 20 dogs.

After 4 weeks, blood flow was observed in 18 dogs. Even after 12 weeks, blood flow was observed in 18 dogs, and it was hence confirmed that the vascular prosthesis has an extremely high patency rate. The length of the sample upon the removal was 4 cm, and so it was not shortened at all, and neither bending nor deformation was observed.

Example 12

A dried tube was produced in accordance with the same procedure as in Example 11, and the dried tube was then stretched under conditions of an average strain rate of 10%/min in an electric oven preset to a temperature of 380° C. so as to give a length 4.5 times as much as the original length, thereby obtaining an expanded porous PTFE tube. Thereafter, this tube was subjected to the same heat treatment as in Example 11 to impart an irregularity structure that the depth of recessed portions was 50% of the whole wall thickness and a distance between projected portions was 200 to 300 $\mu$m to the outer surface of the expanded porous PTFE tube. As a result, an expanded porous PTFE tube having an average fibril length of 45 $\mu$m, an inner diameter of 4 mm and a thickness of 700 $\mu$m at the projected portions was obtained.

The average number of branchings of the nodes in this expanded porous PTFE tube was measured and found to be 4.5 per node. A vascular prosthesis sample composed of this expanded porous PTFE tube was substitutively implanted into carotid arteries of 18 dogs. After 4 weeks, blood flow was observed in 11 dogs. Even after 12 weeks, blood flow was observed in 9 dogs, and it was hence confirmed that the vascular prosthesis has a high patency rate.

Example 13

A dried tube was produced in accordance with the same procedure as in Example 11, and the dried tube was then stretched under conditions of an average strain rate of 16%/min in an electric oven preset to a temperature of 380° C. so as to give a length 7.0 times as much as the original length, thereby obtaining an expanded porous PTFE tube. Thereafter, this tube was subjected to the same heat treatment as in Example 11 to impart an irregularity structure that the depth of recessed portions was 50% of the whole wall thickness and a distance between projected portions was 200 to 300 $\mu$m to the outer surface of the expanded porous PTFE tube. As a result, an expanded porous PTFE tube having an average fibril length of 65 $\mu$m, an inner diameter of 4 mm and a thickness of 700 $\mu$m at the projected portions was obtained.

The average number of branchings of the nodes in this expanded porous PTFE tube was measured and found to be 6.0 per node. A vascular prosthesis sample composed of this expanded porous PTFE tube was substitutively implanted into carotid arteries of 25 dogs. Even after 12 weeks, blood flow was observed in 20 dogs, and it was hence confirmed that the vascular prosthesis has an extremely high patency rate.

Comparative Example 1

After 25 parts by weight of a liquid lubricant (naphtha) were mixed as an auxiliary with 100 parts by weight of PTFE fine powder (product of Daikin Chemical Co., Ltd.), and they were got intimate with each other for at least 24 hours, the mixture was extruded through a ram extruder into a tubular form, and then dried at 60° C. The extruded tube thus obtained was stretched under conditions of an average strain rate of 30%/min in an electric oven preset to a temperature of 480° C. so as to give a length 5.5 times as much as the original length, thereby obtaining an expanded porous PTFE tube. A stainless steel bar having an outer diameter of 4 mm was inserted into the lumen of this expanded porous PTFE tube, and the tube thus treated was passed at a fixed rate through an electric radiating oven with the core temperature preset at 950° C. in a state that both ends of the tube were fixed, whereby an irregularity structure that the depth of recessed portions was 50% of the whole wall thickness and a distance between projected portions was 200 to 300 $\mu$m was imparted to the outer surface of the expanded porous PTFE tube. As a result, an expanded porous PTFE tube having an average fibril length of 58 $\mu$m, a porosity of 68%, iPABP of 0.08 kg/cm$^2$, a leakage pressure of 0.18 kg/cm$^2$, an inner diameter of 4.0 mm, an outer diameter of 5.0 mm and a thickness of 500 $\mu$m at the projected portions was obtained. The melting point of this expanded porous PTFE tube was 327° C. as measured by DSC, and the tube was completely sintered.

A 2-cm specimen was cut out of this expanded porous PTFE tube to measure a load required for compressing the tube by 2 mm in its axial direction at a crosshead speed of 20 mm/min. As a result, it was 3 gf. A 1-cm specimen was cut out of this expanded porous PTFE tube to measure a load required for compressing the tube by 10% in its radial direction at a rate of 10 mm/min. As a result, it was 12 gf.

The node main axis angle of this expanded porous PTFE tube was measured. As a result, a maximum peak of a histogram was about 60%, and nodes were in a form of a straight line almost perpendicular to the axial direction of the tube. The average number of branchings of the nodes in this expanded porous PTFE tube was 2.1 per node.

This expanded porous PTFE tube was cut into lengths of 4 cm to use their pieces as a sample of a vascular prosthesis. Ten samples were substitutively implanted into respective carotid arteries of 10 beagles (weight: 10 kg). After 4 weeks, blood flow was retained in only 2 beagles (patency rate= 20%). The length of the vascular prosthesis sample removed from each beagle was shortened to 3.5 cm, and the sample was bent as a whole.

Comparative Example 2

An expanded porous PTFE tube was produced in the same manner as in Comparative Example 1 except that the draw ratio upon the stretching was changed to 2.5 times, and evaluated likewise. The patency rate of a vascular prosthesis sample composed of this expanded porous PTFE tube was as low as 20%. However, the length of the sample upon the removal was 4 cm, and so it was not shortened.

Comparative Example 3

An expanded porous PTFE tube was produced in the same manner as in Comparative Example 1 except that the inner diameter/outer diameter of the extruded tube were controlled in such a manner that the inner diameter/outer diameter of the stretched tube were 4.0 mm/5.5 mm, and the average strain rate upon the stretching was changed to 25%, and evaluated likewise. The patency rate of a vascular prosthesis sample composed of this expanded porous PTFE tube was as low as 10%. In addition, the length of the sample upon the removal was shortened to 3.5 cm, and the sample was bent as a whole.

Comparative Example 4

An expanded porous PTFE tube was produced in the same manner as in Comparative Example 1 except that the average strain rate and draw ratio upon the stretching were changed to 30% and 5.0 times, respectively, and evaluated likewise. The patency rate of a vascular prosthesis sample composed of this expanded porous PTFE tube was as poor as 0%. In addition, the length of the sample upon the removal was shortened to 3.5 cm, and the sample was bent as a whole.

Comparative Example 5

A dried tube was produced in accordance with the same procedure as in Example 7, and the dried tube was then stretched under conditions of an average strain rate of 54%/min in an electric oven preset to a temperature of 480° C. so as to give a length 7.0 times as much as the original length, thereby obtaining an expanded porous PTFE tube. Thereafter, an irregularity structure that the depth was 50% of the whole wall thickness and a distance between projected portions was 200 to 300 $\mu$m was imparted to the outer surface of the expanded porous PTFE tube in the same manner as in Example 7. As a result, an expanded porous PTFE tube having an average fibril length of 40 $\mu$m, a fibril length distribution of 25%, iPABP of 0.07 kg/cm$^2$, a leakage pressure of 0.19 kg/cm$^2$, an inner diameter of 4 mm and a thickness of 700 $\mu$m at the projected portions was obtained.

A 2-cm specimen was cut out of this expanded porous PTFE tube to measure a load required for compressing the tube by 2 mm in its axial direction at a crosshead speed of 20 mm/min. As a result, it was 4 gf. A 1-cm specimen was cut out of this expanded porous PTFE tube to measure a load required for compressing the tube by 10% in its radial direction at a rate of 10 mm/min. As a result, it was 15 gf.

The node main axis angle of this expanded porous PTFE tube was measured. As a result, a maximum peak of a histogram was about 65%, and nodes were scarcely joined in the axial direction of the tube and were in a form of a straight line almost perpendicular to the axial direction.

This expanded porous PTFE tube was cut into lengths of 4 cm to use their pieces as a sample of a vascular prosthesis. This sample was implanted into carotid arteries of 20 dogs. After 12 weeks, blood flow was observed in only 2 dogs, and the remainder occluded. The vascular prosthesis sample was poor in penetrated state of cells after its removal. According to an ultrasonic echo test about the vascular prosthesis after 1 to 4 weeks, exudation of blood and serum from the outer surface of the vascular prosthesis was slight to such an extent that it was scarcely observed. Many of the cases where the vascular prosthesis occluded before 12 weeks were occlusion caused by organization failure due to the poor cell penetration.

Figure 6:
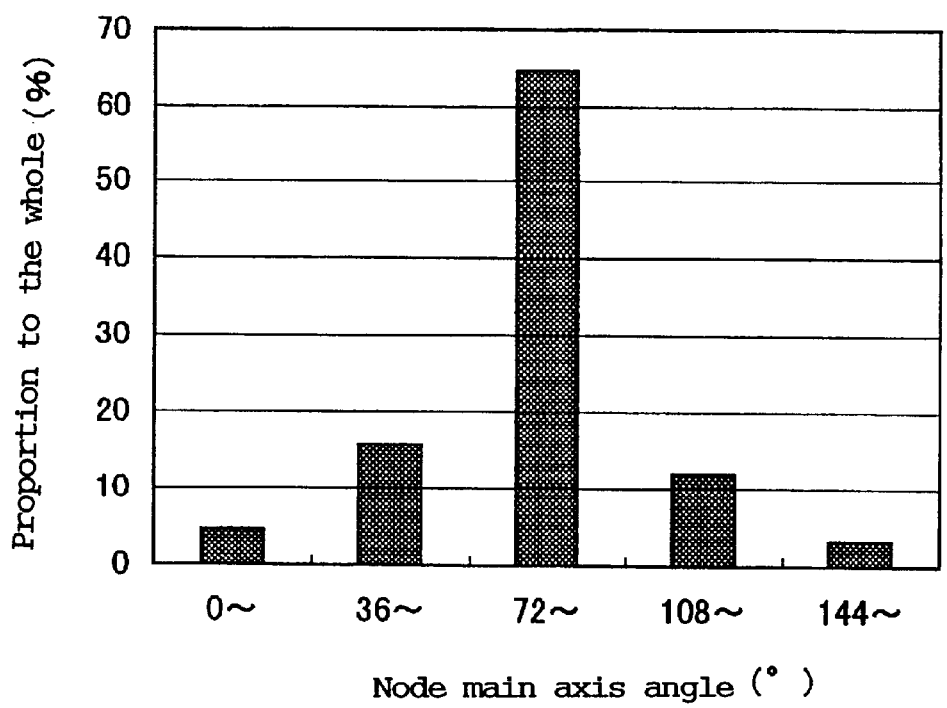
FIG. 6 illustrates a histogram in the case where main axis angles of nodes at 0 to 180° as to an expanded PTFE vascular prosthesis according to Comparative Example 5 are divided into classes of every 36 degrees.

With respect to this expanded porous PTFE tube, a histogram where the node main axis angles at 0 to 180° were classified into classes of every 36° is illustrated in FIG. 6.

Comparative Example 6

A dried tube was produced in accordance with the same procedure as in Example 7, and the dried tube was then stretched under conditions of an average strain rate of 66%/min in an electric oven preset to a temperature of 480° C. so as to give a length 9.0 times as much as the original length, thereby obtaining an expanded porous PTFE tube. Thereafter, an irregularity structure that the depth was 50% of the whole wall thickness and a distance between projected portions was 200 to 300 $\mu$m was imparted to the outer surface of the expanded porous PTFE tube in the same manner as in Example 7. As a result, an expanded porous PTFE tube having an average fibril length of 60 $\mu$m, a fibril length distribution of 28%, iPABP of 0.05 kg/cm$^2$, a leakage pressure of 0.15 kg/cm$^2$, an inner diameter of 4 mm and a thickness of 700 $\mu$m at the projected portions was obtained.

The node main axis angle of this expanded porous PTFE tube was measured. As a result, a maximum peak of a histogram was about 45%, and nodes were observed rarely joining in the axial direction of the tube and were in a form of a straight line almost perpendicular to the axial direction.

A vascular prosthesis sample composed of this expanded porous PTFE tube was implanted into carotid arteries of 15 dogs. After 12 weeks, blood flow was observed in only 3 dogs, and the remainder occluded. The vascular prosthesis sample was good in penetrated state of cells after its removal. However, according to an ultrasonic echo test about the vascular prosthesis after 1 to 4 weeks, exudation of blood and serum from the outer surface of the vascular prosthesis was observed to a great extent. Many of the cases where the vascular prosthesis occluded before 12 weeks were occlusion caused by exudation of blood and serum.

Comparative Example 7

A dried tube was produced in accordance with the same procedure as in Example 7, and the dried tube was then stretched under conditions of an average strain rate of 78%/min in an electric oven preset to a temperature of 480° C. so as to give a length 11.0 times as much as the original length, thereby obtaining an expanded porous PTFE tube.

Thereafter, an irregularity structure that the depth was 50% of the whole wall thickness and a distance between projected portions was 200 to 300 $\mu$m was imparted to the outer surface of the expanded porous PTFE tube in the same manner as in Example 7. As a result, an expanded porous PTFE tube having an average fibril length of 90 $\mu$m, a fibril length distribution of 30%, iPABP of 0.04 kg/cm$^2$, a leakage pressure of 0.10 kg/cm$^2$, an inner diameter of 4 mm and a thickness of 700 $\mu$m at the projected portions was obtained.

The node main axis angle of this expanded porous PTFE tube was measured. As a result, a maximum peak of a histogram was about 70%, and nodes were observed rarely joining in the axial direction of the tube and were in a form of a straight line almost perpendicular to the axial direction.

A vascular prosthesis sample composed of this expanded porous PTFE tube was implanted into carotid arteries of 20 dogs. After 12 weeks, blood flow was observed in only 3 dogs, and the remainder occluded. The vascular prosthesis sample was good in penetrated state of cells after its removal. However, exudation of blood and serum from the outer surface of the vascular prosthesis was observed to a great extent. Many of the cases where the vascular prosthesis occluded before 12 weeks were occlusion caused by exudation of blood and serum.

Comparative Example 8

A dried tube was produced in accordance with the same procedure as in Example 11, and the dried tube was stretched under conditions of an average strain rate of 36%/min in an electric oven preset to a temperature of 480° C. so as to give a length 8.0 times as much as the original length, thereby obtaining an expanded porous PTFE tube. Thereafter, this tube was subjected to the same heat treatment as in Example 11 to impart an irregularity structure that the depth of recessed portions was 50% of the whole wall thickness and a distance between projected portions was 200 to 300 $\mu$m to the outer surface of the expanded porous PTFE tube. As a result, an expanded porous PTFE tube having an average fibril length of 65 μm, an inner diameter of 4 mm and a thickness of 700 μm at the projected portions was obtained.

The average number of branchings of the nodes in this expanded porous PTFE tube was measured and found to be 3.0 per node. A vascular prosthesis sample composed of this expanded porous PTFE tube was substitutively implanted into carotid arteries of 20 dogs. After 12 weeks, blood flow was observed in only 2 dogs, and the remainder occluded.

Comparative Example 9

A tube extruded in accordance with the same procedure as in Example 11 was dried, and the dried tube was stretched under conditions of an average strain rate of 30%/min in an electric oven preset to a temperature of 480° C. so as to give a length 6.0 times as much as the original length, thereby obtaining an expanded porous PTFE tube. Thereafter, this tube was subjected to the same heat treatment as in Example 11 to impart an irregularity structure that the depth of recessed portions was 50% of the whole wall thickness and a distance between projected portions was 200 to 300 μm to the outer surface of the expanded porous PTFE tube. As a result, an expanded porous PTFE tube having an average fibril length of 45 μm, an inner diameter of 4 mm and a thickness of 700 μm at the projected portions was obtained. The average number of branchings of the nodes in this expanded porous PTFE tube was measured and found to be 2.5 per node.

A vascular prosthesis sample composed of this expanded porous PTFE tube was substitutively implanted into carotid arteries of 10 dogs. After 12 weeks, blood flow was observed in only 1 dog, and the remainder occluded.

Comparative Example 10

A dried tube was produced in accordance with the same procedure as in Example 11, and the dried tube was stretched under conditions of an average strain rate of 9%/min in an electric oven preset to a temperature of 380° C. so as to give a length 3.0 times as much as the original length, thereby obtaining an expanded porous PTFE tube. Thereafter, this tube was subjected to the same heat treatment as in Example 11 to impart an irregularity structure that the depth of recessed portions was 50% of the whole wall thickness and a distance between projected portions was 200 to 300 μm to the outer surface of the expanded porous PTFE tube. As a result, an expanded porous PTFE tube having an average fibril length of 35 μm, an inner diameter of 4 mm and a thickness of 700 μm at the projected portions was obtained. The average number of branchings of the nodes in this expanded porous PTFE tube was measured and found to be 6.0 per node. A vascular prosthesis sample composed of this expanded porous PTFE tube was substitutively implanted into carotid arteries of 15 dogs. After 12 weeks, blood flow was observed in only 1 dog, and the remainder occluded.

The experimental results of the above Examples and Comparative Examples are shown in Tables 1 to 6.

TABLE 1

| | Example | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| Stretching temperature (° C.) | 350 | 350 | 350 | 350 | 350 | 350 | 380 | 380 | 380 | 380 | 380 | 380 | 380 |
| Strain rate (%/min) | 8 | 12 | 19 | 8 | 12 | 18 | 12 | 14 | 18 | 10 | 13 | 10 | 16 |
| Draw ratio (times) | 5.5 | 5.5 | 5.5 | 5 | 5 | 9 | 6 | 5 | 7.5 | 8 | 6.5 | 4.5 | 7 |
| Average fibril length (μm) | 58 | 58 | 58 | 50 | 55 | 80 | 60 | 40 | 60 | 80 | 60 | 45 | 65 |
| Porosity (%) | 78 | 77 | 76 | 75 | 78 | 80 | 78 | 76 | 79 | 80 | 78 | 74 | 80 |
| Compressive load in axial direction (gf) | 22 | 17 | 13 | 20 | 26 | 11 | 16 | 23 | 12 | 13 | 13 | 22 | 12 |
| Resistant force to compression in axial direction (gf/mm$^2$) | 3.11 | 2.41 | 1.84 | 1.79 | 1.66 | 1.56 | 1.55 | 2.23 | 1.16 | 1.26 | 1.26 | 2.13 | 1.16 |
| Compressive load in radial direction (gf/cm) | 26 | 23 | 21 | 21 | 19 | 18 | 23 | 24 | 19 | 20 | 23 | 24 | 21 |
| Bubbling point (kg/cm$^2$) | 0.13 | 0.12 | 0.10 | 0.10 | 0.14 | 0.09 | 0.10 | 0.13 | 0.11 | 0.06 | 0.10 | 0.12 | 0.10 |
| Leakage pressure (kg/cm$^2$) | 0.26 | 0.24 | 0.25 | 0.20 | 0.27 | 0.19 | 0.20 | 0.30 | 0.25 | 0.18 | 0.22 | 0.28 | 0.20 |
| Inner diameter/outer diameter (mm) | 4.0/5.0 | 4.0/5.0 | 4.0/5.0 | 4.0/5.5 | 4.0/6.0 | 4.0/5.0 | 4.0/5.4 | 4.0/5.4 | 4.0/5.4 | 4.0/5.4 | 4.0/5.4 | 4.0/5.4 | 4.0/5.4 |

TABLE 2

| | Comparative Example | | | | | | | | | |
|---|---|---|---|---|---|---|---|---|---|---|
| | 1 | 2 | 3 | 4 | 5 | 6 | 7 | 8 | 9 | 10 |
| Stretching temperature (° C.) | 480 | 480 | 480 | 480 | 480 | 480 | 480 | 480 | 480 | 380 |
| Strain rate (%/min) | 30 | 30 | 25 | 30 | 54 | 66 | 78 | 36 | 30 | 9 |
| Draw ratio (times) | 5.5 | 2.5 | 5.5 | 5 | 7 | 9 | 11 | 8 | 6 | 3 |
| Average fibril length (μm) | 58 | 25 | 55 | 55 | 40 | 60 | 90 | 65 | 45 | 35 |
| Porosity (%) | 68 | 65 | 72 | 75 | 74 | 78 | 82 | 72 | 68 | 61 |
| Compressive load in axial direction (gf) | 3 | 20 | 4 | 2 | 4 | 3 | 2 | 8 | 6 | 28 |

TABLE 2-continued

|  | Comparative Example | | | | | | | | | |
|---|---|---|---|---|---|---|---|---|---|---|
|  | 1 | 2 | 3 | 4 | 5 | 6 | 7 | 8 | 9 | 10 |
| Resistant force to compression in axial direction (gf/mm²) | 0.42 | 2.83 | 0.36 | 0.28 | 0.39 | 0.29 | 0.19 | 0.77 | 0.58 | 2.71 |
| Compressive load in radial direction (gf/cm) | 12 | 19 | 12 | 11 | 15 | 11 | 9 | 10 | 14 | 23 |
| Bubbling point (kg/cm²) | 0.08 | 0.12 | 0.09 | 0.07 | 0.07 | 0.05 | 0.04 | 0.07 | 0.10 | 0.18 |
| Leakage pressure (kg/cm²) | 0.18 | 0.20 | 0.19 | 0.16 | 0.19 | 0.15 | 0.10 | 0.16 | 0.19 | 0.33 |
| Inner diameter/outer diameter (mm) | 4.0/5.0 | 4.0/5.0 | 4.0/5.5 | 4.0/5.0 | 4.0/5.4 | 4.0/5.4 | 4.0/5.4 | 4.0/5.4 | 4.0/5.4 | 4.0/5.4 |

TABLE 3

|  | Example | | | | | | | | | | | | |
|---|---|---|---|---|---|---|---|---|---|---|---|---|---|
|  | 1 | 2 | 3 | 4 | 5 | 6 | 7 | 8 | 9 | 10 | 11 | 12 | 13 |
| Angle distribution (*1) | 24 | 28 | 30 | 20 | 22 | 38 | 25 | 35 | 30 | 25 | 15 | 27 | 22 |
| Number of branchings of nodes (*2) | 8.3 | 7.9 | 7.8 | 10.2 | 11.2 | 5.2 | 13.0 | 6.6 | 5.8 | 8.3 | 8.5 | 4.5 | 6.0 |
| Surrounded area (× 10² μm²) | 30 | 80 | 150 | 100 | 60 | 220 | 130 | 20 | 180 | 300 | 100 | 50 | 80 |
| Skeleton length (μm) | 1080 | 490 | 280 | 450 | 600 | 330 | 450 | 600 | 240 | 200 | 370 | 580 | 750 |

*1: Maximum value (%) of the histogram of the node main axis angles; class = 5
*2: Branchings/node

TABLE 4

|  | Comparative Example | | | | | | | | | |
|---|---|---|---|---|---|---|---|---|---|---|
|  | 1 | 2 | 3 | 4 | 5 | 6 | 7 | 8 | 9 | 10 |
| Angle distrilution (*1) | 60 | 71 | 63 | 63 | 65 | 45 | 70 | 53 | 58 | 38 |
| Number of branchings of nodes (*2) | 2.1 | 0.8 | 1.8 | 1.3 | 0.9 | 0.8 | 0.5 | 3.0 | 2.5 | 6.0 |
| Surrounded area (× 10² μm²) | 230 | 30 | 200 | 400 | 280 | 650 | 980 | 780 | 340 | 150 |
| Skeleton length (μm) | 120 | 200 | 160 | 90 | 310 | 120 | 70 | 170 | 150 | 340 |

*1: Maximum value (%) of the histogram of the node main axis angles; class = 5
*2: Branchings/node

TABLE 5

|  | Example | | | | | | | | | | | | |
|---|---|---|---|---|---|---|---|---|---|---|---|---|---|
|  | 1 | 2 | 3 | 4 | 5 | 6 | 7 | 8 | 9 | 10 | 11 | 12 | 13 |
| Number of dogs implanted | 10 | 10 | 10 | 10 | 10 | 10 | 20 | 18 | 25 | 25 | 20 | 18 | 25 |
| Number of dogs in a patency state after 4 weeks | 10 | 9 | 8 | 8 | 8 | 7 | 20 | 13 | 20 | 20 | 18 | 11 | 23 |
| Patency rate after 4 weeks (%) | 100 | 90 | 80 | 80 | 80 | 70 | 100 | 72 | 80 | 80 | 90 | 61 | 92 |
| Number of dogs in a patency state after 12 weeks | 8 | 9 | 8 | 7 | 6 | 5 | 18 | 9 | 20 | 15 | 18 | 9 | 20 |
| Patency rate after 12 weeks (%) | 80 | 90 | 80 | 70 | 60 | 50 | 90 | 50 | 80 | 60 | 90 | 50 | 80 |
| Exudated state of serum | Sm | Sm | Sm | No | No | Gr | Sm | No | Sm | Sm | Sm | No | Sm |
| Penetrated state of cells | Ex | Ex | Ex | Gd | Gd | Ex | Ex | Gd | Ex | Ex | Ex | Gd | Ex |

TABLE 6

| | Comparative Example | | | | | | | | | |
|---|---|---|---|---|---|---|---|---|---|---|
| | 1 | 2 | 3 | 4 | 5 | 6 | 7 | 8 | 9 | 10 |
| Number of dogs implanted | 10 | 10 | 10 | 10 | 20 | 15 | 20 | 20 | 10 | 15 |
| Number of dogs in a patency state after 4 weeks | 2 | 2 | 1 | 0 | 6 | 3 | 8 | 6 | 4 | 5 |
| Patency rate after 4 weeks (%) | 20 | 20 | 10 | 0 | 30 | 20 | 40 | 30 | 40 | 33 |
| Number of dogs in a patency state after 12 weeks | 0 | 2 | 0 | 0 | 2 | 3 | 3 | 2 | 1 | 1 |
| Patency rate after 12 weeks (*) | 0 | 20 | 0 | 0 | 10 | 20 | 15 | 10 | 10 | 6.7 |
| Exudated state of serum | Gr | No | Gr | Gr | Sm | Gr | Gr | Gr | Sm | No |
| Penetrated state of cells | Gd | Ua | Gd | Gd | Ua | Gd | Ex | Ex | Ua | Ua |

Figure 7:
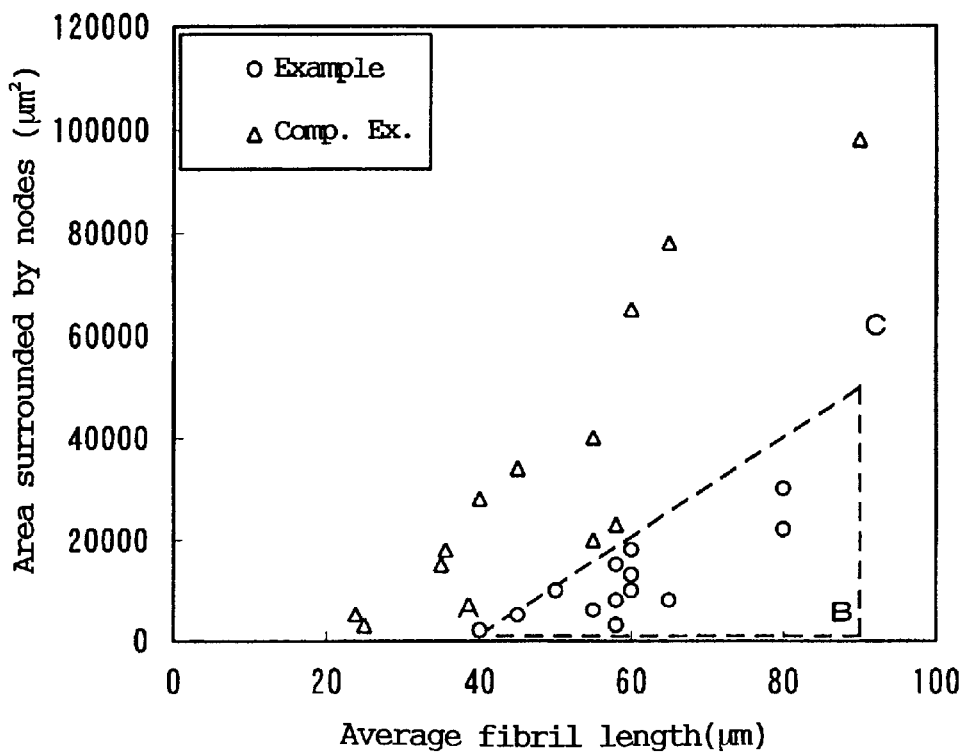
FIG. 7 is a surrounded area graph illustrating the relationship between an average fibril length and an area surrounded by nodes.
Figure 8:
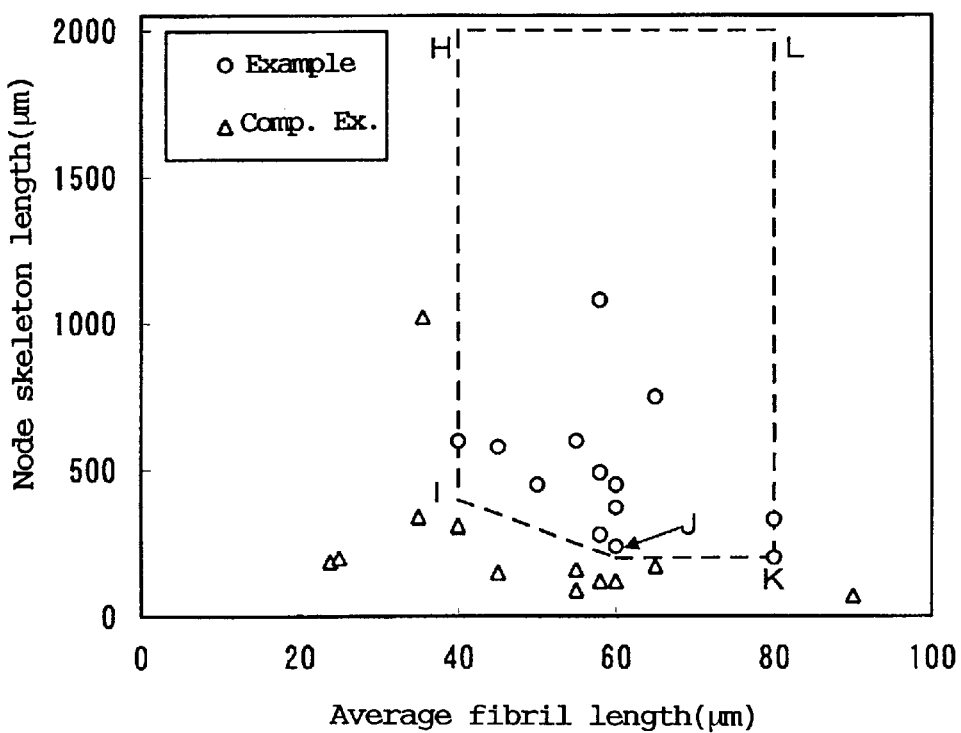
FIG. 8 is a node skeleton length graph illustrating the relationship between an average fibril length and a node skeleton length.

With respect to these Examples and Comparative Examples, a surrounded area graph illustrating the relationship between the average fibril length and the area surrounded by the nodes is shown in FIG. 7, and a node skeleton length graph illustrating the relationship between the average fibril length and the node skeleton length is shown in FIG. 8.

INDUSTRIAL APPLICABILITY

According to the present invention, there are provided prostheses for blood vessels, which are manufactured from an expanded porous PTFE tube having a fine fibrous structure comprising fibrils and nodes connected with one another by said fibrils, have a long average fibril length, a large pore diameter, a high porosity, a excellent effect to facilitate penetration into the vital tissue and sufficient rigidity against compression in axial and radial directions thereof even without reinforcing them and are markedly improved in patency after their implantation into vital bodies.

Small-diameter vascular prostheses made of an expanded porous PTFE tube have heretofore been put to no practical use because they are easy to occlude. On the other hand, the prostheses for blood vessels according to the present invention are suitable for use as small-bore vascular prostheses having an inner diameter less than 6 mm, further not greater than 5 mm, particularly not greater than 4 mm.

What is claimed is:

1. A prosthesis for a blood vessel, which is manufactured from an expanded porous polytetrafluoroethylene tube having a fine fibrous structure comprising fibrils and nodes connected with one another by said fibrils, wherein the tube has the following features:

(A) the average fibril length being at least 40 $\mu$m;
   (B) the porosity being at least 70%;
   (C) a load required for compressing the tube by 10% in its axial direction at a strain rate of 100%/min being at least 10 gf; and
   (D) a resistant force per unit sectional area of the tube produced upon the 10% compression being at least 1.0 gf/mm$^2$.

2. The prosthesis for a blood vessel according to claim 1, wherein the tube further has a feature: (E) a load per unit length of the tube required for compressing the tube by 10% in its radial direction at a strain rate of 200%/min is preferably at least 15 gf/cm.

3. The prosthesis for a blood vessel according to claim 1, wherein in a histogram of 5 classes prepared within a range of 0 to 180° as to node main axis angles as measured on the luminal surface and outer peripheral surface of the tube and at least 5 cylindrical curved surfaces present between them and concentric with the luminal surface, each class does not exceed ⅖ in a proportion to the whole.

4. The prosthesis for a blood vessel according to claim 3, wherein in the histogram, each class does not exceed ⅓ in a proportion to the whole.

5. The prosthesis for a blood vessel according to claim 1, wherein the average number of branchings of the nodes as measured on the luminal surface and outer peripheral surface of the tube and at least 5 cylindrical curved surfaces present between them and concentric with the luminal surface is at least 4.0.

6. The prosthesis for a blood vessel according to claim 1, wherein in a surrounded area graph that the average fibril length expressed by the unit of $\mu$m is regarded as an x-axis, and an area expressed by the unit of $\mu$m$^2$ surrounded by the nodes as measured on the luminal surface and outer peripheral surface of the tube and at least 5 cylindrical curved surfaces present between them and concentric with the luminal surface is regarded as a y-axis, the average fibril length and the area surrounded by the nodes fall within a region formed by connecting 3 points of a point A where x is 40 and y is 1000, a point B where x is 90 and y is 1000 and a point C where x is 90 and y is 50000.

7. The prosthesis for a blood vessel according to claim 6, wherein in the surrounded area graph, the average fibril length and the area surrounded by the nodes fall within a region formed by connecting 3 points of a point D where x is 40 and y is 2000, a point E where x is 80 and y is 2000 and a point F where x is 80 and y is 40000.

8. The prosthesis for a blood vessel according to claim 1, wherein in a node skeleton length graph that the average fibril length expressed by the unit of $\mu$m is regarded as an x-axis, and a skeleton length expressed by the unit of $\mu$m of the nodes as measured on the luminal surface and outer peripheral surface of the tube and at least 5 cylindrical curved surfaces present between them and concentric with the luminal surface is regarded as a y-axis, the average fibril length and the node skeleton length fall within a region formed by connecting 5 points of a point H where x is 40 and y is 2000, a point I where x is 40 and y is 400, a point J where x is 60 and y is 200, a point K where x is 80 and y is 200 and a point L where x is 80 and y is 2000.

9. The prosthesis for a blood vessel according to claim 8, wherein in the node skeleton length graph, the average fibril length and the node skeleton length fall within a region formed by connecting 5 points of a point M where x is 40 and y is 2000, a point N where x is 40 and y is 500, a point P where x is 60 and y is 200, a point Q where x is 80 and y is 200 and a point R where x is 80 and y is 2000.

10. The prosthesis for a blood vessel according to claim 1, wherein the tube has an inner diameter which is less than 6 mm.

11. The prosthesis for a blood vessel according to claim 1, wherein the node has an average length of which is at least 3 times the average fibril length.

12. The prosthesis for a blood vessel according to claim 1, wherein the tube has a leakage pressure which is at least 0.15 kgf/cm$^2$.

13. The prosthesis for a blood vessel according to claim 1, wherein the tube has a bubble point which is at least 0.05 kgf/cm$^2$ as measured with isopropyl alcohol.

* * * * *